US007339023B2

(12) United States Patent
Mayo et al.

(10) Patent No.: US 7,339,023 B2
(45) Date of Patent: *Mar. 4, 2008

(54) PARTIAL PEPTIDE MIMETICS AND METHODS

(75) Inventors: Kevin H. Mayo, Minneapolis, MN (US); Thomas R. Hoye, St. Paul, MN (US); Carolee Flader-Lavey, New Providence, NJ (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/346,504

(22) Filed: Feb. 2, 2006

(65) Prior Publication Data
US 2006/0128629 A1 Jun. 15, 2006

Related U.S. Application Data

(63) Continuation of application No. 10/371,406, filed on Feb. 20, 2003, now Pat. No. 7,056,514.

(60) Provisional application No. 60/359,272, filed on Feb. 20, 2002.

(51) Int. Cl.
C07K 1/00 (2006.01)
(52) U.S. Cl. .................................... 530/300
(58) Field of Classification Search ................ 530/300
See application file for complete search history.

(56) References Cited

U.S. PATENT DOCUMENTS

| 5,089,274 | A | 2/1992 | Marra et al. |
|---|---|---|---|
| 5,171,739 | A | 12/1992 | Scott |
| 5,190,873 | A | 3/1993 | Lernhardt et al. |
| 5,198,541 | A | 3/1993 | Elsbach et al. |
| 5,334,584 | A | 8/1994 | Scott et al. |
| 5,348,942 | A | 9/1994 | Little, II et al. |
| 5,595,887 | A | 1/1997 | Coolidge et al. |
| 5,639,725 | A | 6/1997 | O'Reilly et al. |
| 5,786,324 | A | 7/1998 | Gray et al. |
| 5,830,860 | A | 11/1998 | Gray et al. |
| 5,837,678 | A | 11/1998 | Little, II |
| 5,837,682 | A | 11/1998 | Folkman et al. |
| 5,854,205 | A | 12/1998 | O'Reilly et al. |
| 5,854,214 | A | 12/1998 | Little, II |
| 5,856,302 | A | 1/1999 | Ammons et al. |
| 5,955,577 | A | 9/1999 | Mayo |
| 6,486,125 | B1 | 11/2002 | Mayo |
| 7,030,087 | B2 | 4/2006 | Gray et al. |
| 7,056,514 | B2 | 6/2006 | Mayo et al. |
| 7,144,982 | B2 | 12/2006 | Mayo |
| 2002/0146406 | A1 | 10/2002 | Mayo |
| 2003/0153502 | A1 | 8/2003 | Gray et al. |
| 2004/0053828 | A1 | 3/2004 | Mayo et al. |
| 2005/0118678 | A1 | 6/2005 | Mayo |
| 2006/0183191 | A1 | 8/2006 | Gray et al. |

| 2007/0010438 | A1 | 1/2007 | Mayo et al. |

FOREIGN PATENT DOCUMENTS

| WO | WO 89/01486 | 2/1989 |
|---|---|---|
| WO | WO 90/09183 | 8/1990 |
| WO | WO 92/09621 | 6/1992 |
| WO | WO 92/09695 | 6/1992 |
| WO | WO 93/05797 | 4/1993 |
| WO | WO 93/23434 | 11/1993 |
| WO | WO 94/17819 | 8/1994 |
| WO | WO 94/18323 | 8/1994 |
| WO | WO 94/20532 | 9/1994 |
| WO | WO 94/25476 | 11/1994 |
| WO | WO 95/00641 | 1/1995 |
| WO | WO 95/01428 | 1/1995 |
| WO | WO 95/02414 | 1/1995 |
| WO | WO 96/31528 | 10/1996 |
| WO | WO 96/37212 | 11/1996 |
| WO | WO 97/44354 | 11/1999 |
| WO | WO 01/53335 A2 | 7/2001 |
| WO | WO 03/070751 A2 | 8/2003 |
| WO | WO 2005/042699 A2 | 5/2005 |
| WO | WO 2006/01038 A1 | 1/2006 |
| WO | WO 2006/042104 | 4/2006 |

OTHER PUBLICATIONS

Altieri et al., "Association of Biomolecular Systems via Pulsed Field Gradient NMR Self-Diffusion Measurements," *J. Am. Chem. Soc.*, 117, 7566-7567 (1995).

Anisowicz et al., "Constitutive overexpression of a growth-regulated gene in transformed Chinese hamster and human cells," *Proc. Natl. Acad. Sci. USA*, 84, 7188-7192 (1987).

Bangalore et al., "Identification of the Primary Antimicrobial Domains in Human Neutrophil Cathepsin G," *J. Biol. Chem.*, 265(23), 13584-13588 (1990).

Battafarano et al., "Peptide derivatives of three distinct lipopolysaccharide binding proteins inhibit lipopolysaccharide-induced tumor necrosis factor-a secretion in vitro", Surgery 1995; 118:318-324.

Bax et al., "MLEV-17-Based Two-Dimensional Homonuclear Magnetization Transfer Spectroscopy," *J. Magnetic Resonance*, 65, 355-360 (1985).

Beamer et al., "Crystal Structure of Human BPI and Two Bound Phospholipids at 2.4 A Resolution", Science, 276, 1861-1864 (1997).

(Continued)

*Primary Examiner*—Mark Navarro
(74) *Attorney, Agent, or Firm*—Mueting Raasch & Gebhardt, P.A.

(57) ABSTRACT

Partial peptide mimetics and methods of making and using, wherein the partial peptide mimetics have a first amino acid sequence comprising ANIKLSVQMKL (SEQ ID NO:8), a homolog thereof, or a segment of SEQ ID NO:8 or a homolog thereof, a second amino acid sequence comprising IIVKLND (SEQ ID NO:2), a homolog thereof, or a segment of SEQ ID NO:2 or a homolog thereof, and a β-turn inducing scaffold bonded between the first and second amino acid sequences.

25 Claims, 5 Drawing Sheets

OTHER PUBLICATIONS

Bekele et al., "Improved Synthesis of the Boc and Fmoc Derivatives of 4-(2'-Aminoethyl)-6-dibenzofuranpropionic Acid: An Unnatural Amino Acid That Nucleates .beta.-Sheet Folding" J. Org. Chem., 62, 2259-2262 (1997).

Blanco et al., "A short linear peptide that folds into a native stable β-hairpin in aqueous solution," Structural Biology, 1, 584-590 (1994).

Boehm et al., "Antiangiogenic Therapy of Experimental Cancer does not Induce Acquired Drug Resistance", Nature, 390, 404-407 (1997).

Bone et al., "A second large controlled clinical study of E5, a monoclonal antibody to endotoxin: Results of a prospective, multicenter, randomized, controlled trial," Critical Care Medicine, 23, 994-1005 (1995).

Bottone et al., "Association of Pseudomonas cepacia with Chronic Granulomatous Disease," J. Clin. Microbiol., 1(5), 425-428 (1975).

Brown et al., "[8] Chemical Synthesis and Cloning of a Tyrosine tRNA Gene," Methods in Enzymology, 68, 109-151 (1979).

Brunger, X-Plor Manual, Yale University Press, New Haven (1992).

Bryson et al., "Protein Design: A Hierarchic Approach," Science, 270, 935-941 (1995).

Budson et al., Biochem. Biophys. Res. Comm., 225, 141-145 (1996).

Campanelli et al., "Azurocidin and a Homologous Serine Protease from Neutrophils—Differential Anticmicrobial and Proteolytic Properties," J. Clin. Invest., 85, 904-915 (1990).

Cantor et al., "The behavior of biological macromolecules," Biophysical Chemistry, Part III, 979-1039 (1980).

Capone, "Screening Recombinant Baculovirus Plaques In Situ with Antibody Probes," Gene Anal. Techn., 6, 62-66 (1989).

Carpino, "I-Hydroxy-7-azabeiizotriazole. An Efficient Peptide Coupling Additive,"J. Am. Chem. Soc., 115, 4397-4398 (1993).

Casey et al., "Neisseria Gonorrhoeae Survive Intraleukocytic Oxygen—Independent Antimicrobial Capacities of Anaerobic and Aerobic Granulocytes in the Presence of Pyocin Lethal for Extracellular Gonococci". Infect. Immun.52:384-389 (1986).

Chen et al., "Characterization of the WW domain of the human Yes-associated protein and its polyproline-containing ligands" J. Biol. Chem. 272:17070, 1997.

Cody et al., Int. Surg. Res., 52:315, 1992.

Dahlberg et al., "A Novel Endotoxin Antagonist Attenuates Tumor Necrosis Factorα Secretion," Journal of Surgical Research, 63, 44-48 (1996).

D'Amato et al., "Thalidomide is an Inhibitor of Angiogenesis," Proc. Natl. Acad. Sci. USA, 91(9):4082-4085 (1994).

Dameron et al., "Control of Angiogenesis in Fibroblasts by p53 Regulation of Thrombospondin-1," Science, 265:1582-1584 (1994).

Daopin et al., "Crystal Structure of Transforming Growth Factor-Beta 2: An Unusual Fold for the Superfamily", Science, 257, 369-373 (1992).

Delaglio et al., "NMRPipe: a multidimensional spectral processing system basedon UNIX pipes", J. Biomol. NRM, 6, 277-293 (1995).

Deuel et al., "Amino acid sequence of human platelet factor 4," Proc. Natl. Acad. Sci. USA, 74, 2256-2258 (1977).

Diaz et al., "Design, Synthesis, and Partial Characterization of Water-Soluble β-sheets stabilized by a Dibenzofuran-Based Amino Acid", J. Am. Chem. Soc., 115, 3790-3791 (1993).

Dikler et al., "Improving Mass Spectrometric Sequencing of Arginin Containing Peptides by Derivatization with Acetylacetone" J. Mass. Spectrom. 32:1337, 1997.

Dings et al., "The designed angiostatic peptide anginex synergistically improves chemotherapy and antiangiogenesis therapy with angiostatin" Cancer Res., 63, 382-385 (2003).

Dings et al., "on the Road to a Small Molecule Mimetic of the Peptide Anginex, a Potent Anti-Angiogenic, Anti-tumor Agent" Abstract #5361, Presented Apr. 6-10, 2002 American Association for Cancer Research, San Francisco, CA. Published Proceedings of the American Association for Cancer Research, vol. 43, pp. 1083, Mar. 2002.

Dintzis et al., "A Comparison of the Immunogenicity of a Pair of Enantiomeric Proteins," Proteins: Structure, Function, and Genetics, 16(3), 306-308 (1993).

Dugas et al., Bioorganic Chemistry, Springer-Verlag, New York, NY (1981), Title Page, Copyright Page, Table of Contents, and pp. 54-92.

Dunn et al., "Efficacy of type specific and cross reactive murine monoclonal antibodies directed against endotoxin during experimental sepsis", Surgery, 98:283, 1985.

Eck et al., "The Structure of Human Lymphotoxin (Tumor Necrosis Factor-Beta) at 1.9 A Resolution", J. Biol. Chem., 267, 2119-2122 (1992).

Elsbach et al., "Bactericidal/permeability increasing protein and host defense against Gram-negative bacterial and endotoxin," Curr. Opn. in Imm., 5(1), 103-107 (1993).

Farley et al., "Lipopolysaccharide Structure Determines Ionic and Hydrophobic Binding of a Cationic Antimicrobial Neutrophil Granule Protein," Infect. Immun., 56, 1589-1592 (1988).

Fields et al., in Synthetic Peptides: A User's Guide, W.M. Freeman & Company, New York, NY, pp. 77-183 (1992).

Folkman et al., "Angiogenesis in Cancer, Vascular, Rheumatoid and other Disease", Nature Med., 1, 27-31 (1995).

Folkman, "What is the evidence that tumors are angiogenesis dependent", J. Natl. Cancer. Inst., 82, 4-6 (1990).

Folkman et al., "Angiogenesis" J. Biol. Chem., 267, 10931-10934 (1992).

Gabay et al., "Antibiotic proteins of human polymorphonuclear leukocytes," PNAS USA, 86, 5610-5614 (1989).

Gallin et al., "Recent Advances in Chronic Granulomatous Disease," Ann. Int. Med., 99, 657-674 (1983).

Gazzano-Santoro et al., "High-Affinity Binding of the Bactericidal/Permeability-Increasing Protein and a Recombinant Amino-Terminal Fragment to the Lipid A Region of Lipopolysaccharide," Infect. Immun., 60(11), 4754-4761 (1992).

Gibbs et al., "A PFG NMR Experiement for Accurate Diffusion and Flow Studies in the Presence of Eddy Currents", J. Magnetic Resonance, 93:395-402 (1991).

Gray et al., "Cloning of the cDNA of a Human Neutrophil Bactericidal Protein," J. Biol. Chem., 264(16), 9505-9509 (1989).

Gray, "Killing Pseudomonas by a Granule Protein from PMNL," Grant No. 1R01AI026159-01, Awarded by the National Institutes of Health. 1988 (Abstract Only).

Gray, "Metabolic Stimulation and Bactericidal Function of Polymorphonuclear Leukocytes," J. Retic. Soc., 22(2):87-88 (1977).

Griffioen et al., "Anginex, a designed Peptide that Inhibits Angiogenesis", Biochem. J., 354, 233-242 (2001).

Griffioen et al., "Tumor Angiogenesis Is Accompanied by a Decreased Inflammatory Response of Tumor-Associated Endothelium," Blood, 88(2):667-673 (1996).

Griffioen et al., "Endothelial ICAM-1 expression is suppressed in human malignancies; role of angiogenic factors" Cancer Res., 56, 1111-1117 (1996).

Griffioen et al., "Tumor Angiogenesis Is Accompanied by a Decreased Inflammatory Response of Tumor-Associated Endothelium," Proc. Am. Ass. Cancer Res., 37:55, Abstract No. 380 (1996).

Groenewegen et al., "Supernatants of Human Leukocytes Contain Mediator, Different From Interferon γ, Which Induces Expression of MHC Class II Antigens," J. Exp. Med., 164:131-143 (1986).

Gupta et al., "A potent inhibitor of endothelial cell proliferation is a generated by proteolytic cleavage of the chemokine platelet factor 4," PNAS USA, 92, 7799-7803 (1995).

Gupta et al., "Inhibition of Endothelial Cell Proliferation by Platelet Factor—4 Involves a Unique Action on S Phase Progression", J. Cell Biol., 127, 1121-1127 (1994).

Hancock, "Alterations in Outer Membrane Permeability," Ann. Rev. Microbiol., 38, 237-264 (1984).

Harlow et al., Eds., Antibodies: A Laboratory Manual, Cold Spring Harbor Laboratory (1988), Title Page, Copyright Page, and Table of Contents.

Hartree, "Determination of Protein: A Modification of the Lowry Method That Gives a Linear Photometric Response," *Analytical Biochem.*, 48, 422-427 (1972).

Hendsch et al., "Do salt bridges stabilize proteins? A continuum electrostatic analysis," *Protein Science*, 3, 211-226 (1994).

Heumann et al., "Competition between Bactericidal/Permeability-Increasing Protein and Lipopolysaccharide-Binding Protein for Lipopolysaccharide Binding to Monocytes," *J. Infect. Dis.*, 167(6), 1351-1357 (1993).

Hoess et al., "Crystal structure of an endotoxin-neutralizing protein from the horseshoe crab, *Limulus* anti-LPS factor, at 1 6 Åresolution," *EMBO J.*, 12(9), 3351-3356 (1993).

Hohenester et al., "Crystal Structure of the Angiogenesis Inhibitor Endostatin at 1.5 A Resolution" EMBO J., 17, 1656-1664 (1998).

Holmes et al., "Studies of the metabolic Activity of Leukocytes from Patients with a Genetic Abnormality of Phagocytic Function". J. Clin. Invest, 46:1422-1432 (1976).

Holmes et al., "Fatal Granulomatous Disease of Childhood," *Lancet*, 1, 1225-1228 (1966).

Holmes, "Metabolic Stimulation and Bactericidal Function of Polymorphonuclear Leukocytes", Reticulo. Soc., 22:87-88 (1978).

Holt et al., "Biochemistry of α Granule Proteins," *Seminars in Hematology*, 22(2), 151-163 (1985).

Homma, "A New Antigenic Schema and Live-cell Slide-agglutination Procedure for the Infrasubspecific, Serologic Classification of *Pseudomonas aeruginosa*," *Japan J. Exp. Med.*, 46,(6), 329-336 (1976).

Hovde et al., "Physiological Effects of a Bactericidal Protein from Human Polymorphonuclear Leukocytes on *Pseudomonas aeruginosa*," *Infect. Immun.*, 52(1), 90-95 (1986).

Hovde et al., "Characterization of a Protein from Normal Human Polymorphonuclear Leukocytes with Bactericidal Activity against *Pseudomonas aeruginosa*," *Infect. Immun.*, 54(1), 142-148 (1986).

Ilyina et al., "Synthetic Peptides Probe Folding Initiation Sites in Platelet Factor-4: Stable Chain Reversal Found within the Hydrophobic Sequence LIAT*LKNGR*KISL," *Biochemistry*, 33 13436-13444 (1994).

Ilyina et al., "Multiple native-like conformations trapped via self-association-induced hydrophobic collapse of the 33-residue β-Sheet domain from platelet factor 4," *Biochem. J.*, 306, 407-419 (1995).

Ilyina et al., "NMR Structure of a de Novo Designed, Peptide 33mer with Two Distinct, Compact β-Sheet Folds," *Biochemistry*, 36(17):5245-5250 (1997).

Jameson et al., "A rationally designed CD4 analogue inhibits experimental allergic encephalomyelitis," *Nature*, 368, 744-746 (1994).

Jeener et al., "Investigation of exchange processes by two-dimensional NMR spectroscopy," *J. Chem. Phys.*, 71(11), 4546-4553 (1979).

Johnston, Jr., et al., "Chronic Granulomatous Disease," *The Pediatric Clinics of North America*, 24(2), 365-376 (1977).

Johnston, "Molecular Science Sets Its Sights on Septic Shock," *J. NIH Res.*, 3(10), 61-65 (1991).

Jones et al., "Structure of Tumour Necrosis Factor Nature", 338, 225-228 (1989).

Kambic et al., "Biomaterials in Artificial Organs," C&EN, 64(2):30-48 (1986).

Kelly. "The Alternative Conformations of Amyloidogenic Proteins and their Multi-Step Assembly Pathways" Curr. Opin. Struct. Biol. 8:101, 1998.

Kelly et al., "Bioorganic Chemistry and Neurochemistry", Skaggs Scientific Report 1997-1998—Investigators' Reports (3 pages).

Kelly. "Amyloid Fibril Formation and Protein Misassembly: A Structural Quest for Insights into Amyloid and Prion Diseases" Structure 5:595, 1997.

Kelly. "The Environmental Dependency of Protein Folding Best Explains Prion and Amyloid Diseases" Proc. Natl. Acad. Sci. USA 95:930, 1997.

Kelly et al., "Role of bactericidal permeability—increasing protein in the treatment of gram-negative pneumonia," *Surgery*, 114(2), 140-146 (1993).

Kelly et al., "Transthyretin Quatemary and Tertiary Structural Changes Facilitate Misassembly into Amyloid: A New Therapeutic Strategy Based on Preventing the Amyloidoge conformational changes" Adv. Protein Chem. 50:161, 1997.

Kim et al., "Thermodynamic β-sheet propensities measured using a zinc-finger host peptide,", *Nature*, 362, 267-270 (1993).

King et al., "A cleavage method which minimizes side reactions following Fmoc solid phase peptide synthesis" Int. J. Pept. Protein. Res., 36, 255-266 (1990).

Kitayama et al., "Suppressive effect of basic fibroblast growth factor on transendothelial emigration of $CD4^{30}$ T-lymphocyte", Cancer Res., 54, 4729-4733 (1994).

Kyte et al., "A Simple Method for Displaying the Hydropathic Character of a Protein," *J. Mol. Biol.*, 157, 105-132 (1982).

Lai et al., "GdnHCI-Induced denaturation and refolding of transthy exhibits a marked hysteresis: Equilibria with high kinetic barriers" Biochemistry 36:10230, 1997.

Larrick et al. "Polymerase Chain Reaction Using Mixed Primers: Cloning of Human Monoclonal Antibody Variable Region Genes from Single Hybridoma Cells". Bio/Tech, 7:934-938 (1989).

Lasdun et al., "Inhibition of Endopeptidase 24.15 Slows the in Vivo Degradation of Luteinizing Hormone-Releasing Hormone," *J. of Pharm. and Exp. Therapeutics*, 251(2), 439-447 (1989).

Lehrer et al., "Defensins: Antimicrobial and Cytotoxic Peptides of Mammalian Cells," *Annu. Rev. Immunol.*, 11, 105-28 (1993).

Liekens et al., Angiogenesis: regulators and clinical applications. J. Biochem. Pharm., 61, 253-270 (2001).

Little et al., "Functional Domains of Recombinant Bactericidal/Permeability Increasing Protein ($rBPI_{23}$)," *J. Biol. Chem.*, 269, 1865-1872 (1994).

Luckow et al., "Trends in the Development of Baculovirus Expression Vectors," *Bio/Technology*, 6, 47-55 (1988).

Luster et al., "The IP-10 Chemokine Binds to a Specific Cell Surface Heparan Sulfate Site Shared with Platelet Factor 4 and Inhibits Endothelial Cell Proliferation", J. Exp. Med., 182, 219-231 (1995).

Mandell, "Bactericidal Activity of Aerobic and Anaerobic Polymorphonuclear Neutrophils," *Infect. Immun.*, 9(2), 337-341 (1974).

Mannion et al., "Separation of Sublethal and Lethal Effects of the Bactericidal/Permeability Increasing PRotein on *Escherichia coli*," *J. Clin. Invest.*, 85, 853-860 (1990).

Marion et al., "Application of Phase Sensitive Two-Dimensional Correlated Spectroscopy (COSY) for Measurements of $^1H$-$^1H$ Spin-Spin Coupling Constants in Proteins,", *Biochemical and Biophysical Research Communications*, 113(3), 967-974 (1983).

Marra et al., "Bactericidal/Permeability-Increasing Protein has Endotoxin-Neutralizing Activity," *J. Immunol.*, 144(2), 662-666 (1990).

Marra et al., "The Role of Bactericidal/Permeability-Increasing Protein as a Natural Inhibitor of Bacterial Endotoxin," *J. Immunol.*, 148(2), 532-537 (1992).

Martinotti et al., "Heavy-metal Modulation of the Human Intercellular Adhesion Molecule (ICAM-1) Gene Expression," *BBA—Gene Structure and Expression*, 1261:107-114 (1995).

Mayer et al., "Declining Severity of First Attack of Rheumatic Fever," *Amer. J. Dis. Chil.*, 105, 146-152 (1963).

Mayo et al., Designed β-Sheet Peptides that Inhibit Proliferation and Induce Apoptosis in Endothelial Cells. Angiogenesis, 4, 45-51 (2001).

Mayo et al., "NMR Solution Structure of the 32 kD Tetrameric Platelet Factor-4 ELR-Motif N-terminal Chimer: A Symmetric Tetramer", Biochemistry, 34, 11399-11409 (1995).

Mayo et al. "Designed β-sheet-forming peptide 33mers with potent human bactericidal/permeability increasing protein-like bactericidal and endotoxin neutralizing activities", (1998) Biochimica et Biophysica Acta 1425, 81-92.

Mayo et al., "Structure-function relationships in novel peptide dodecamers with broad-spectrum bactericidal and endotoxin-neutralizing activities",(2000) *Biochem J.* 349, 717-728.

Mayo, "Peptide Based Antiagiogenic Antitumor Agent," Grant No. 1R01CA096090-01, Awarded by the National Institutes of Health. 2002 (Abstract Only).

Mayo et al., "Design of a Partial Peptide Mimetic of Anginex with Antiangiogenic and Anticancer Activity," Journ. Of Biological Chemistry, 2003, vol. 278, No. 45, pp. 45746-45742.

McCloskey et al., "Treatment of Septic Shock with Human Monoclonal Antibody HA-1A," *Ann. Inter. Med.*, 121, 1-5 (1994).

Melder et al., During angiogenesis, vascular endothelial growth factor and basic fibroblast growth factor regulate natural killer cell adhesion to tumor endothelium Nature Med., 2, 992-997 (1996).

Miller et al., "Biology and Biochemistry of the Chemokines: A Family of Chemotactic and Inflammatory Cytokines," *Critical Reviews in Immunology*, 12(1,2) 17-46 (1992).

Minor, Jr. et al., "Context is a major determinant of β-sheet propensity," *Nature*, 371, 264-267 (1994).

Minor, Jr. et al., "Measurement of the β-sheet-forming propensities of amino acids,", *Nature*, 367, 660-663 (1994).

Mire Sluis et al., "Implications for the Assay and Biological Activity of Interleukin-8: Results of a WHO International Collaborative Study" J. Immunol. Methods, 200, 1-16 (1997).

Molema et al., "Rocking the Foundations of Solid Tumor Growth by Attacking the Tumor's Blood Supply", Immunol. Today, 19, 392-394 (1998).

Mossman, "Rapid Colorimetric Assay for Cellular Growth and Surivival: Application to Proliferation and CytotoxicityAssays," *Journal of Immunological Methods*, 65(1-2), 55-63 (1983).

Nettleton et al., "Protein Subunit interactions and structural integrity of amyloidogenic transthyretins: Evidence from Electrospray Mass Spectrometry" J. Mol. Biol. 1998 281:553-564.

Okamura et al., "Outer Membrane Mutants of *Salmonella typhimurium* LT2 Have Lipopolysaccharide-Dependent Resistance to the Bactericidal Activity of Anaerobic Human Neutrophils," *Infect. Immun.*, 36(3), 1086-1095 (1982).

Ooi et al., "A 25-kDa $NH_2$-terminal Fragment Carries All the Antibacterial Activities of the Human Neutrophil 60-kDa Bactericidal/Permeability-increasing Protein," *J. Biol. Chem.*, 262(31), 14891-14894 (1987).

Ooi et al., "Endotoxin-neutralizing Properties of the 25 kD N-Terminal Fragment and a Newly Isolated 30 kD C-Terminal Fragment of the 55-60 kD Bactericidal/Permeability-increasing Protein of Human Neutrophils," *J. Exp. Med.*, 174, 649-655 (1991).

O'Reilly et al., "Endostatin: an Endogenous Inhibitor of Angiogenesis and Tumor Growth", Cell, 88, 277-285 (1997).

O'Reilly et al., "Angiostatin: a Novel Angiogenesis Inhibitor that Mediates the Suppression of Metastases by a Lewis Lung Carcinoma", Cell, 79, 315-328 (1994).

Otzen et al., "Side-Chain Determinants of β-Sheet Stability," *Biochemistry*, 34(17), 5718-5724 (1995).

Palombella et al.,:Mitogenic and Cytotoxic Actions of Tumor Necrosis Factor in BALB/c 3T3 Cells. The Role of Phospholipase Activation, J. Biol. Chem., 264, 18128-18136 (1989).

Pereira et al., "Synthetic bactericidal peptide based on CAP37: A 37-kDa human neutrophil granule-associated cationic antimicrobial protein chemotactic for monocytes," PNAS USA, 90, 4733-4737 (1993).

Piali et al., "Endothelial vascular cell adhesion molecule 1 expression is suppressed by melanoma and carcinoma" J. Exp. Med., 181, 811-816 (1995).

Piantini et al., "Multiple Quantum Filters for Elucidating NMR Coupling Networks," *J. Am. Chem. Soc.*, 104, 6800-6801 (1982).

Pike et al., "Vasostatin, a Calreticulin Fragment, Inhibits Angiogenesis and Supresses Tumor Growth", J. Exp. Med., 188, 2349-2356 (1998).

Piotto et al., Gradient-tailored Excitation for Single-quantum NMR Spectroscopy of Aqueous Solutions J. Biomol. NMR, 2, 661-665 (1992).

Priestle et al., "Crystallographic Refinement of Interleukin-1-beta at 2.0 A Resolution", Proc. Natl. Acad. Sci. USA, 86, 9667-9671 (1989).

Quie et al., "In Vitro Bactericidal Capacity of Human Polymorphonuclear Leukocytes: Diminished Activity in Chronic Granulomatous Disease of Childhood," *J. Clin. Invest.*, 46(4), 668-679 (1967).

Quinn et al., "Betadoublet: De novo design, synthesis, and characterization of a β-sandwich protein," PNAS USA, 91, 8747-8751 (1994).

Rest, "Killing of *Neisseria gonorrhoeae* by Human Polymorphonuclear Neutrophil Granule Extracts," *Infect. Immun.*, 25(2), 574-579 (1979).

Richardson et al., "The de novo design of protein structures," TIBS, 14, 6 pp. (Jul. 1989).

Richardson et al., "Looking at proteins: representations, folding, packing, and design," *Biophysical Journal*, 63, 1186-1209 (1992).

Robaye et al., "Tumor Necrosis Factor Induces Apoptosis in Normal Endothelial Cells in Vitro", Am. J. Pathol., 138, 447-453 (1991).

Rucker et al. "Z-filtered DIPSI-2" Mol. Phys., 68, 509-517 (1989).

Rustici et al., "Molecular Mapping and Detoxification of the Lipid A Binding Site by Synthetic Peptides," Science, 259, 361-365 (1993).

Sambrook et al., (Eds.), *Molecular Cloning: A Laboratory Manual, 2nd Edition*, Cold Spring Harbor Laboratory Press (1989), Title Page and Table of Contents.

Sato et al., "Actions of Tumor Necrosis Factor on Cultured Vascular Endothelial Cells: Morphologic Modulation, Growth Inhibition and Cytotoxicity", Japan Natl. Cancer Inst., 76, 1113-1121 (1986).

Searle et al., "A short linear peptide derived from the N-terminal sequence of ubiquitin folds into a water-stable non-native β-hairpin," Nature Structural Biology, 2(11), 999-1006 (1995).

Shafer et al., "Lipid A and Resistance of *Salmonella typhimurium* to Antimicrobial Granule Proteins of Human Neutrophil Granulocytes," *Infect. Immun.*, 43(3), 834-838 (1984).

Shafer et al., "Cationic Antimicrobial Proteins from Human Neutrophil Granulocytes in the Presence of Diisopropyl Fluorophosphate," *Infect. Immun.*, 45(1), 29-35 (1984).

Shafer et al., "Synthetic Peptides of Human Lysosomal Cathespin G with Potent Antipseudomonal Activity," *Infect. Immun.*, 61(5), 1900-1908 (1993).

Shaka et al., "Iterative Schemes for Bilinear Operators: Applications to Spin Decoupling" J. Magn. Reson., 77, 274-293 (1988).

Shinefield et al., "Bacterial Interference: Its Effect on Nursery-Acquired Infection with *Staphylococcus aureus*," *Amer. J. Dis. Children.* 105:146, 1963.

Siefferman et al., "*Pseudomonas aeruginosa* Variants Isolated from Patients with Cystic Fibrosis are Killed by a Bactericidal Protein from Human Polymorphonuclear Leukocytes", Infect. Immun. 59:2152-2157 (1991).

Smith et al., "Guidelines for Protein Design: The Energetics of β Sheet Side Chain Interactions," Science, 270, 980-982 (1995).

Smith et al., "A Thermodynamic Scale for the β-Sheet Forming Tendencies of the Amino Acids," *Biochemistry*, 33, 5510-5517 (1994).

Spitznagel et al., "Antibiotic Proteins of Human Neutrophils," *J. Clin. Invest.*, 86(5), 1381-1386 (1990).

States et al., "A Two-Dimensional Nuclear Overhauser Experiment with Pure Absorption Phase in Four Quadrants," *J. Magnetic Resonance*, 48, 286-292 (1982).

Stewart et al., *Solid phase peptide synthesis*, 2nd ed. Rockford, Illinois, Pierce Chemical Co. pp. 125-135 (1984).

Su et al., "In Vitro Stability of Growth Hormone Releasing Factor (GRF) Analogs in Porcine Plasma," *Horm. Metab. Res.*, 23, 15-21 (1991).

Summers et al., *A Manual of Methods for Baculovirus Vectors and Insect Cell Culture Procedures*, Title Page, Copyright Page, and Table of Contents (1987).

Tanimura et al., "Determinants of protein side-chain packing," *Protein Science*, 3, 2358-2365 (1994).

Taraboletti et al., "Inibition of Angiogenesis and Murine Hemangioma Growth by Batimastat, a Synthetic Inhibitor of Matrix Metalloproteinases," *J. Natl. Cancer. Inst.*, 87(4):293-298 (1995).

Tolsma et al., "Peptides Derived from Two Separate Domains of the Matrix Protein Thrombospondin-1 Have Antiangiogenic Activity", J. Cell Biol., 122, 497-511 (1993).

Tsang et al., "Hydrophobic Cluster Formation is Necessary for Dibenzofuran-Based Amino Acids to Function as β-Sheet Nucleators", J. Am. Chem. Soc., 116, 3988-4005 (1994).

Uknis et al., "Design of a Potent Novel Endotoxin Antagonist," *Surgery*, 122(2):380-385 (1997).

Van der Schaft et al., "Bactericidal Permeability Increasing Protein (BPI) inhibits Angiogenesis via Induction of Apoptosis in Vascular Endothelial Cells", Blood, 96, 176-181 (2000).

Van der Schaft et al., "The Designer Anti-Angiogenesis Peptide Anginex Targets Tumor Endothelial Cells and Inhibits Tumor Growth in Animal Models" FASEB J., 16, 1991-1993 (2002).

Verma, "Improved Genomic Blot Hybridization," Bio/Tech., 7, 934 (1989).

Wang et al., "Direct double-stranded DNA sequencing with baculovirus genomes," *J. Virol. Meth.*, 31, 113-118 (1991).

Wasiluk et al., "Comparison of Granule Proteins from Human Polymorphonuclear Leukocytes Which Are Bactericidal toward *Pseudomonas aeruginosa*," *Infect. Immun.*, 59(11), 4193-4200 (1991).

Weiss et al., "Purification and Characterization of a Potent Bactericidal and Membrane Active Protein from the Granules of Human Polymorphonuclear Leukocytes," *J. Biol. Chem.*, 253, 2664-2672 (1978).

Weiss et al., "Killing of Gram-Negative Bacteria by Polymorphonuclear Leukocytes," *J. Clin. Invest.*, 69, 959-970 (1982).

Weiss et al., "Role of Charge and Hydrophobic Interactions in the Action of the Bactericidal/Permeability-increasing Protein of Neutrophils on Gram-negative Bacteria", J. Clin. Invest., 71(3), 540-549 (1983).

Weiss et al., "Environmental Modulation of Lipopolysaccharide Chain Length Alters the Sensitivity of *Escherichia coli* to the Neutrophil Bactericidal/Permeability-Increasing Protein," *Infect. Immun.*, 51(2), 594-599 (1986).

Weiss et al., "Human Bactericidal/Permeability-increasing Protein and a Recombinant $NH_2$-Terminal Fragment Cause Killing of Serum-resistant Gram-negative Bacterial in Whole Blood and Inhibit Tumor Necrosis Factor Release Induced by the Bacteria," *J. Clin. Invest.*, 90, 1122-1130 (1992).

Wills et al., "Concentration Dependence of the Diffusion Coefficient of a Dimerizing Protein: Bovine Pancreatic Trypsin Inhibitor," *J. Phys. Chem.*, 85, 3978-3984 (1981).

Wider et al., "Homonuclear Two-Dimensional H NMR of Proteins. Experimental Procedures" J. Magn. Reson., 56, 207-234 (1985).

Wild et al., "Quantitative Assessment of Angiogenesis and Tumor Vessel Architecture by Computer-Assisted Digital Image Analysis: Effects of VEGF-Toxin Conjugate on Tumor Microvessel Density", Microvasc. Res., 59, 368-376 (2000).

Yan et al., "Engineering of betabellin 14D: Disulfide-induced folding of a β-sheet protein," *Protein Science*, 3, 1069-1073 (1994).

Dings et al., "β-Sheet is the bioactive conformation of the antiangiogenic anginex peptide," Biochem. J. 2003, 373:281-288.

Stahura et al., "Molecular scaffold-based design and comparison of combinatorial libraries focused on the ATP-binding site of protein kinases," Journ. Of Molecular Graphics and Modeling 17, 1-9, 1999.

B
```
         H¹⁵ L
         R   K
         K   W
         F   K    D-C(=O)-NH₂
         L   I²⁰  L
         K¹⁰ I    S
         M   V    L³⁰
         Q   K    E
         V   L    R
         S   N    G
         L⁵      D
         K
         I
         N
  ⁺H₃N-A¹
```

C

A

B

□ polar, hydrophilic side chains
○ non-polar, hydrophobic side chains

PARTIAL PEPTIDE MIMETICS AND METHODS

CROSS-REFERENCE TO RELATED APPLICATION

The present application is a continuation application under 37 CFR § 1.53(b) of Ser. No. 10/371,406, Confirmation No. 9367, filed on Feb. 20, 2003 (now U.S. Pat. 7,056,514, issued on Jun. 6, 2006), entitled PARTIAL PEPTIDE MIMETICS AND METHODS, which is a non-provisional application of U.S. Provisional Patent Application Ser. No. 60/359,272, filed on Feb. 20, 2002, each of which is incorporated herein by reference in its entirety.

STATEMENT OF GOVERNMENT RIGHTS

This work was supported in part by the U.S. Department of Defense (Army) under Grant Number DA/DAMD17-99-1-9564 and the U.S. National Cancer Institute under Grant Number R01 CA-96090. The government may have certain rights in the invention.

BACKGROUND

Angiogenesis, the process of new blood vessel formation, is key to normal organ development, as well as to various pathological disorders like cancer, arthritis, diabetic retinopathy and restenosis (A. W. Griffioen et al., *Biochem. J.*, 354, 233-242 (2001)). βpep-25, which has the sequence ANIKLSVQMKLFKRHLKWKIIVKLNDGRELSLD (SEQ ID NO:1), a designed cytokine-like β-sheet-forming peptide 33mer, is an anti-angiogenic compound being developed to combat these pathological disorders (K. H. Mayo et al., *Angiogenesis*, 4, 45-51 (2001); and S. Liekens et al., *J. Biochem. Pharm.*, 61, 253-270 (2001)).

The use of agents that can inhibit angiogenesis, particularly in anti-tumor research (e.g., M. S. O'Reilly et al., *Cell*, 88, 277-285 (1997); and T. Boehm et al., *Nature*, 390, 404-407 (1997)), has indicated that anti-angiogenic therapy will be a promising therapeutic modality in the near future. To date, the search for angiogenic inhibitors has been focused on controlling two of the processes that promote angiogenesis: endothelial cell (EC) growth and adhesion (G. Molema et al., *Immunol. Today*, 19, 392-394 (1998); and J. Folkman et al., *Nature Med*, 1, 27-31 (1995). Targeting EC as an anti-tumor treatment is attractive primarily because EC are more accessible than are other cells to pharmacologic agents delivered via the blood, and EC are genetically stable and are not easily mutated into drug resistant variants.

Most anti-angiogenic agents have been discovered by identifying endogenous molecules, primarily proteins, which inhibit EC growth. This traditional approach has produced a number of anti-angiogenics, such as platelet factor-4 (PF4), thrombospondin, tumor necrosis factor-α (TNF-α, depending on its concentration), interferon-γ inducible protein-10, angiostatin, endostatin and vasostatin and bactericidal-permeability increasing (BPI) protein. See, for example, M. S. O'Reilly et al., *Cell*, 88, 277-285 (1997); S. K. Gupta et al., *J. Cell Biol.*, 127, 1121-1127 (1994); S. S. Tolsma et al., *J. Cell Biol.*, 122, 497-511 (1993); N. Sato et al., *Japan Natl. Cancer Inst.*, 76, 1113-1121 (1986); V. J. Palombella et al., *J. Biol. Chem.*, 264, 18128-18136(1989); B. Robaye et al., *Am. J. Pathol.*, 138, 447-453 (1991); A. D. Luster et al., *J. Exp. Med*, 182, 219-231 (1995); M. S. O'Reilly et al., *Cell*, 79, 315-328 (1994); S. E. Pike et al., *J. Exp. Med*, 188, 2349-2356 (1998); and D. W. J. Van der Schaft et al., *Blood*, 96, 176-181 (2000). About forty anti-angiogenic agents are currently known.

Most anti-angiogenic proteins are compositionally similar, having a relatively high incidence of hydrophobic and positively charged residues and are folded primarily as β-sheets (A. R. Mire Sluis et al., *J. Immunol. Methods*, 200, 1-16 (1997)): interleukin-1 (IL-1), tumor necrosis factor (TNF), lymphotoxin (LT or TNF-β), transforming growth factor-β (TGF-β), endostatin. See, for example, J. P. Priestle et al., *Proc. Natl. Acad. Sci. USA*, 86, 9667-9671 (1989); E. Y. Jones et al., *Nature*, 338, 225-228 (1989); M. J. Eck et al., *J. Biol. Chem.*, 267, 2119-2122 (1992); S. Daopin et al., *Science*, 257, 369-373 (1992); and E. Hohenester et al., *EMBO J.*, 17, 1656-1664 (1998).

Recently, a designed amphipathic β-sheet-forming peptide 33mer, βpep-25 was shown to be a potent inhibitor of EC growth and angiogenesis. βpep-25 is more effective at inhibiting EC growth than PF4 and several other well-known angiogenesis inhibitors such as angiostatin, endostatin, AGM-1470 and thrombospondin-1. βpep-25 is believed to act by specifically blocking adhesion and migration of angiogenically-activated EC, leading to apoptosis and ultimately to inhibition of angiogenesis in vitro and in vivo and inhibits tumor growth by up to 80% in various models. See, for example, D. W. J. Van der Schaft et al., *Faseb J.*, 16, 1991-1993 (2002); and R. P. Dings et al., *Cancer Res.*, 63, 382-385 (2003).

For the smart design of smaller compounds, the identification of specific amino acid residues and their spatial relationships are used. One of the main goals among structural biologists and pharmaceutical chemists is to develop small molecules and potentially more effective anti-tumor agents. Nevertheless, for anti-angiogenic proteins such structure-activity relationships (SAR), i.e., specific residues and conformations which impart activity, are sorely needed, and even the analysis of high-resolution molecular structures of a number of anti-angiogenic proteins, e.g., endostatin, PF4, and BPI, has yet to provide this information. See, for example, E. Hohenester et al., *EMBO J.*, 17, 1656-1664 (1998); K. H. Mayo et al., *Biochemistry*, 34, 11399-11409 (1995); and L. J. Beamer et al., *Science*, 276, 1861-1864 (1997).

SUMMARY

From the structures of angiogenesis inhibitors that are known it appears that most anti-angiogenic proteins are compositionally similar. They show a relatively high incidence of hydrophobic and positively charged residues and a β-sheet. βpep-25 also falls into this category as an amphipathic β-sheet-forming peptide 33-mer. It is believed that this β-sheet conformation is necessary for the bioactivity of the 33-mer βpep-25. The present invention is directed to the identification of specific residues and conformations that are responsible for activity, leading to the design of partial peptide mimetics of βpep-25.

As used herein, a peptide mimetic is a compound that mimics a peptide. The use of the adjective "partial" indicates that it is not a full mimetic because it contains some peptide segments, i.e., amino acids in a sequence.

The present invention relates to partial peptide mimetics and methods for using such compounds that include segments (i.e., portions) of the βpep-25 sequence, which is ANIKLSVQMKLFKRHLKWKIIVKLNDGRELSLD (SEQ ID NO:1), or homologs thereof.

In particular, the partial peptide mimetics of the present invention are designed to include all or segments of the sequences ANIKLSVQMKL (SEQ ID NO:8) or a homolog thereof, and IIVKLND (SEQ ID NO:2) or a homolog thereof, with a β-turn inducing scaffold bonded therebetween (e.g., covalently bonded). Segments of these sequences (SEQ ID NO:8 and SEQ ID NO:2 or homologs thereof) include one or more amino acids. Segments of SEQ ID NO:8 and SEQ ID NO:2 as well as homologs of the segments and the full sequences preferably provide the partial peptide mimetic with at least one of the following activities: inhibition of endothelial cell proliferation in vitro at an IC50 level of less than 80 μM; inhibition of angiogenesis in vitro at a level of less than 85% sprouting in a collagen gel-based assay; or reduction in tumor volume in vivo (e.g., in an animal model) by at least 25% relative to a control at the end of an administration period.

In certain embodiments, segments of SEQ ID NO:8 or homologs thereof preferably include at least three amino acids of SEQ ID NO:8 or homologs thereof (preferably, contiguous amino acids), and more preferably include at least six amino acids of SEQ ID NO:8 or homologs thereof (preferably, contiguous amino acids). In certain embodiments, segments of SEQ ID NO:8 or homologs thereof include those in which deletions have been made at the N-terminus preferably by 1, 2, 3, 4, 5, 6, 7, or 8 residues, more preferably by 1, 2, 3, 4, or 5 residues. Examples of segments of SEQ ID NO:8 that can be used in forming the partial peptide mimetics of the present invention include MKL, QMKL (SEQ ID NO:4), SVQMKL (SEQ ID NO:5), IKLSVQMKL (SEQ ID NO:6), and NIKLSVQMKL (SEQ ID NO:7). Particularly preferred such segments include, for example, SVQMKL (SEQ ID NO:5), IKLSVQMKL (SEQ ID NO:6), and NIKLSVQMKL (SEQ ID NO:7).

In certain embodiments, segments of SEQ ID NO:2 or homologs thereof include at least one amino acid of SEQ ID NO:2 or homologs thereof, and preferably at least four amino acids of SEQ ID NO:2 or homologs thereof (preferably, contiguous amino acids). In certain preferred embodiments, segments of SEQ ID NO:2 or homologs thereof include those in which deletions have been made at the C-terminus by 1, 2, 3, 4, 5, or 6 residues. Particularly preferred segments of SEQ ID NO:2 that can be used in forming the partial peptide mimetics of the present invention include I, IIVK (SEQ ID NO:3), and IIVKLN (SEQ ID NO:9).

The β-turn inducing scaffold can be a chemical scaffold, such as a dibenzofuran-containing scaffold.

Particularly preferred partial peptide mimetics of the present invention include at least the 7 amino acids IIVKLND (SEQ ID NO:2) in combination with at least the 4 amino acids QMKL (SEQ ID NO:4) with a β-turn inducing scaffold, such as a chemical scaffold like a dibenzofuran-containing scaffold, bonded therebetween. Other preferred partial peptide mimetics include at least SEQ ID NO:2 and at least the 6 amino acids SVQMKL (SEQ ID NO:5) with a β-turn inducing scaffold bonded therebetween. Other preferred partial peptide mimetics include at least SEQ ID NO:2 and at least the 9 amino acids IKLSVQMKL (SEQ ID NO:6) with a β-turn inducing scaffold bonded therebetween. Other preferred partial peptide mimetics include at least SEQ ID NO:2 and at least the 10 amino acids NILKSVQMKL (SEQ ID NO:7) with a β-turn inducing scaffold bonded therebetween. Other preferred partial peptide mimetics include at least SEQ ID NO:2 and at least the 11 amino acids ANILKSVQMKL (SEQ ID NO:8) with a β-turn inducing scaffold bonded therebetween.

Other preferred partial peptide mimetics include at least ANIKLSVQMKL (SEQ ID NO:8) and at least the amino acid I with a β-turn inducing scaffold bonded therebetween. Other preferred partial peptide mimetics include at least SEQ ID NO:8 and at least the 4 amino acids IIVK (SEQ ID NO:3) with a β-turn inducing scaffold bonded therebetween. Other preferred partial peptide mimetics include at least SEQ ID NO:8 and at least the 6 amino acids IIVKLN (SEQ ID NO:9) with a β-turn inducing scaffold bonded therebetween.

Other preferred partial peptide mimetics include at least SVQMKL (SEQ ID NO:5) and at least the amino acid I with a β-turn inducing scaffold therebetween. Other preferred partial peptide mimetics include at least SEQ ID NO:5 and at least the 6 amino acids IIVKLN (SEQ ID NO:9) with a β-turn inducing scaffold bonded therebetween.

This invention also relates to methods of using at least one of the partial peptide mimetics disclosed herein. Preferably, the methods are for treatment of various conditions in vivo, although in vitro methods are also desirable. Typically, such methods involve the use of a composition that includes at least one of the partial peptide mimetics and optionally a carrier, preferably a pharmaceutically acceptable carrier.

Such methods include, for example, treating a bacterial infection or endotoxic shock. In one embodiment, the partial peptide mimetic neutralizes endotoxin, in another the partial peptide mimetic is bactericidal, and in another the partial peptide mimetic is both bactericidal and neutralizes endotoxin. Such partial peptide mimetics can also be used to inhibit bacterial infection or endotoxic shock in a cell culture.

This invention also relates to a method for inhibiting TNF-α levels, inhibiting endothelial cell proliferation, promoting inter-cellular adhesion molecule (ICAM) expression, inhibiting inter-cellular adhesion molecule (ICAM) expression down regulation, inhibiting tumorigenesis, and inhibiting angiogenesis. Such methods can be carried out in vivo (e.g., for treating a mammal) or in vitro (e.g., in a cell culture). Similarly, such partial peptide mimetics can be used to inhibit pathologic disorders such as atherosclerosis, restenosis, diabetic retinopathy, neovascular glaucoma, rheumatoid arthritis, and endometriosis.

As used herein, "a," "an," "the," "at least one," and "one or more" are used interchangeably.

"Amino acid" is used herein to refer to a chemical compound with the general formula: $NH_2$—CRH—COOH, where R, the side chain, is H or an organic group. Where R is organic, R can vary and is either polar or nonpolar (i.e., hydrophobic). The amino acids of this invention can be naturally occurring or synthetic (often referred to as non-proteinogenic). As used herein, an organic group is a hydrocarbon group that is classified as an aliphatic group, a cyclic group or combination of aliphatic and cyclic groups. The term "aliphatic group" means a saturated or unsaturated linear or branched hydrocarbon group. This term is used to encompass alkyl, alkenyl, and alkynyl groups, for example. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" refers to mono- or polycyclic aromatic hydrocarbon groups. As used herein, an organic group can be substituted or unsubstituted. One letter and three letter symbols are used herein to designate the naturally occurring amino acids. Such designations including R or Arg, for Arginine, K or Lys, for Lysine, G or Gly, for Glycine, and X for an undetermined amino acid, and the like, are well known to those skilled in the art.

The terms "polypeptide" and "peptide" as used herein are used interchangeably and refer to a compound that includes two or more amino acids. These terms do not connote a specific length of amino acids (e.g., herein, an "amino acid sequence" can include just one amino acid).

The term "partial peptide mimetic" is used herein to refer to a compound that mimics a peptide, and contains some peptide segments, i.e., amino acids in a sequence. At times these compounds are simply referred to as "peptides" or "polypeptides."

The following abbreviations are used throughout the application:

| | |
|---|---|
| A = Ala = Alanine | T = Thr = Threonine |
| V = Val = Valine | C = Cys = Cysteine |
| L = Leu = Leucine | Y = Tyr = Tyrosine |
| I = Ile = Isoleucine | N = Asn = Asparagine |
| P = Pro = Proline | Q = Gln = Glutamine |
| F = Phe = Phenylalanine | D = Asp = Aspartic Acid |
| W = Trp = Tryptophan | E = Glu = Glutamic Acid |
| M = Met = Methionine | K = Lys = Lysine |
| G = Gly = Glycine | R = Arg = Arginine |
| S = Ser = Serine | H = His = Histidine |

Other abbreviations used herein include: DBF, dibenzofuran; EC, endothelial cell; EAM, endothelial adhesion molecule; HUVEC, human umbilical vein EC; PBS, phosphate buffered saline; HPLC, high performance liquid chromatography; bFGF, basic fibroblast growth factor; VEGF, vascular endothelial growth factor; PF4, platelet factor-4; BPI, bactericidal-permeability increasing protein; NMR, nuclear magnetic resonance; GC-LRMS, gas chromatography-liquid chromatography mass spectrometry; IR, infrared spectroscopy; SPPS, solid phase peptide synthesis; BOP/HOBT, benzotriazol-1-yloxy)tris(dimethylamino)phosphonium hexafluorophosphate/1-hydroxybenzotriazole; DPC, dodecylphosphocholine.

BRIEF DESCRIPTION OF THE DRAWINGS

FIG. 1(A). Sequences for the dodecapeptide walk-throughs below the amino acid sequence of βpep-25. Proliferation of bFGF-stimulated (10 ng/ml) human umbilical vascular EC (HUVEC) cultures was measured by quantification of $^3$H-thymidine incorporation. Proliferation is expressed as mean counts per minute (cpm) of quadruplicate cultures in three independent experiments (±SEM). EC proliferation results from alanine scanning (tested at 25 µM dose) are expressed in bar graph format as the percentage of proliferating EC (the arithmetic mean counts per minute (cpm) of triplicate cultures) relative to control cultures. For walk-through peptides, results are given as $IC_{50}$ values from dose response curves; only $IC_{50}$ values for dodecapeptides with significant activity relative to βpep-25 are given.

FIG. 1(B). Overall fold for βpep-25 (3 β-strands with 2 turns), shows with functionally key residues boxed-in.

FIG. 1(C) shows the parent DBF analog (11DBF7 or CF-8) with the introduction of the scaffold.

In FIG. 4(A) treatment was initiated at the time of inoculation with MA148 cells. In FIG. 4(B) an intervention study is shown where tumors were allowed to establish to a palpable size before treatment was initiated. In either study, control groups of animals were treated with PBS containing human serum albumin to control for protein content. Tumor volumes (for all groups n=11, ± SEM) are plotted as mm$^3$ vs. days post inoculation. The inserts show the body weight development of the mice during the study as a measurement of overall toxicity.

DETAILED DESCRIPTION OF ILLUSTRATIVE EMBODIMENTS OF THE INVENTION

Figure 1:
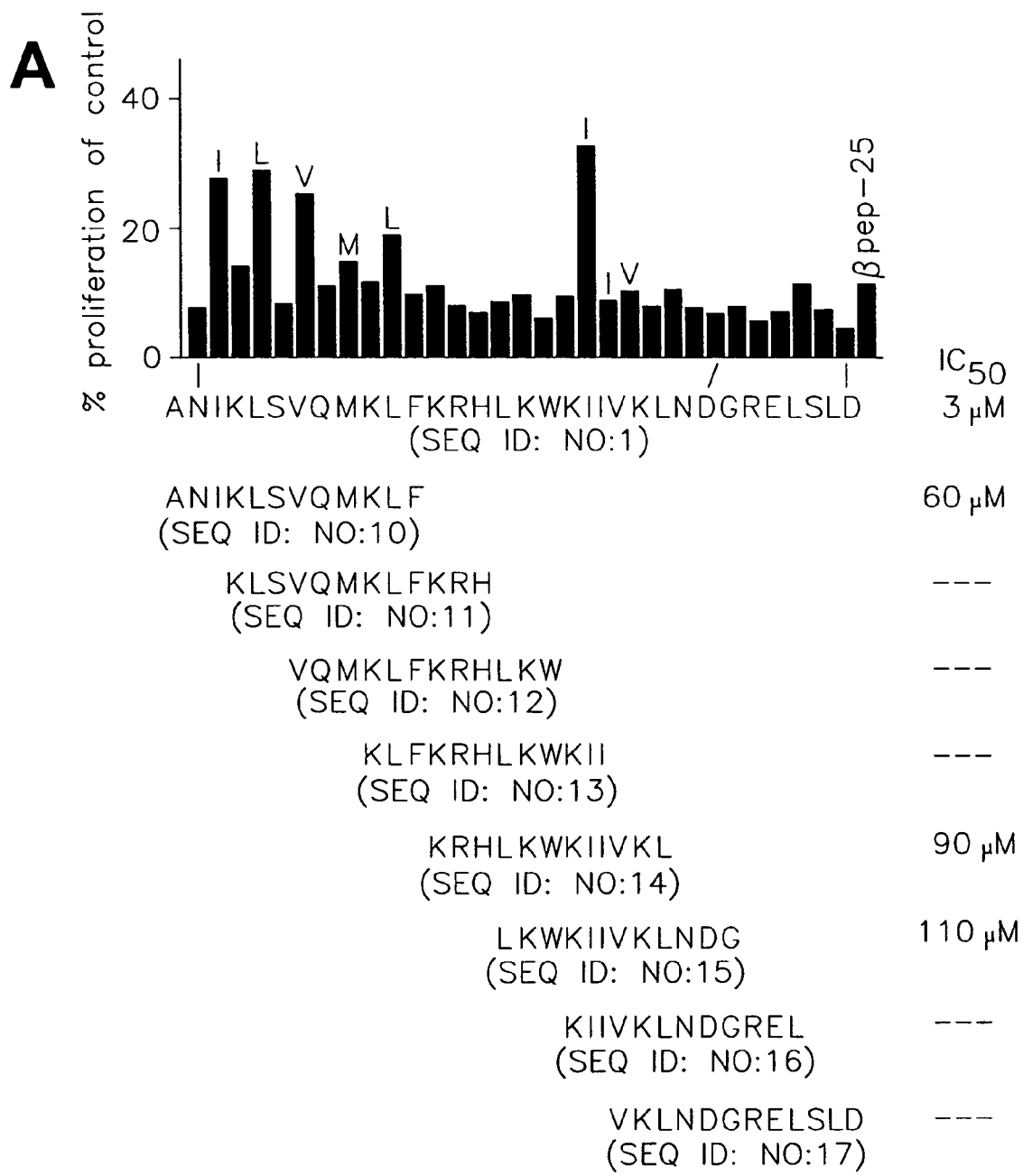
Figure 1:
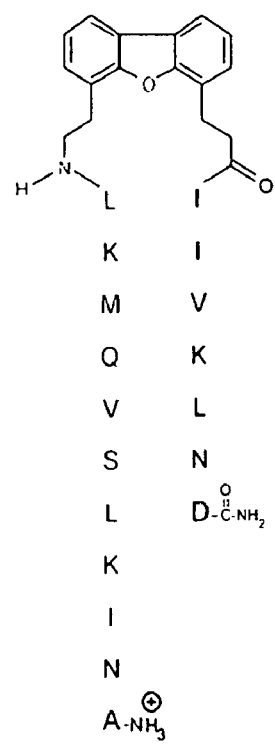

The present invention provides partial peptide mimetics and methods of using such partial peptide mimetics. These partial peptide mimetics include segments (i.e., portions) of the βpep-25 sequence, which is ANIKLSVQMKLFKRHLKWKIIVKLNDGRELSLD (SEQ ID NO:1), or homologs thereof. These partial peptide mimetics preferably include at least 7 amino acid residues. Although there is no upper limit to the number of amino acid residues, it is desirable for the partial peptide mimetics to be small and approach the size of conventional therapeutic small organic molecules.

In particular, the partial peptide mimetics of the present invention are designed to include all or segments of the sequences ANIKLSVQMKL (SEQ ID NO:8) or a homolog thereof, and IIVKLND (SEQ ID NO:2) or a homolog thereof, with a β-turn inducing scaffold bonded therebetween (e.g., covalently bonded). Segments of these sequences (SEQ ID NO:8 and SEQ ID NO:2 or homologs thereof) include one or more amino acids.

Segments of SEQ ID NO:8 and SEQ ID NO:2 as well as homologs of the segments and the full sequences preferably provide the partial peptide mimetic with at least one of the following activities: inhibition of endothelial cell proliferation in vitro at an IC50 level of less than 80 µM (more preferably less than 50 µM, and even more preferably less than 25 µM) as determined using the assay described in the Examples Section; inhibition of angiogenesis in vitro at a level of less than 85% sprouting (more preferably less than 75% sprouting, even more preferably 50% sprouting, and even more preferably less than 35% sprouting) as determined using the collagen gel-based assay described in the Examples Section; or reduction in tumor volume in vivo by at least 25% (more preferably by at least 50%, and even more preferably by at least 70%) relative to a control at the end of an administration period as determined using the assay with an animal model described in the Examples Section. These values can be determined by one of skill in the art and are typically average values.

In certain embodiments, segments of SEQ ID NO:8 or homologs thereof preferably include at least three amino acids of SEQ ID NO:8 or homologs thereof (preferably, contiguous amino acids), and more preferably include at least six amino acids of SEQ ID NO:8 or homologs thereof (preferably, contiguous amino acids). In certain embodiments, segments of SEQ ID NO:8 or homologs thereof include those in which deletions have been made at the N-terminus preferably by 1, 2, 3, 4, 5, 6, 7, or 8 residues, more preferably by 1, 2, 3, 4, or 5 residues, and even more preferably by 5 residues. Examples of segments of SEQ ID NO:8 that can be used in forming the partial peptide mimetics of the present invention include MKL, QMKL (SEQ ID NO:4), SVQMKL (SEQ ID NO:5), IKLSVQMKL (SEQ ID NO:6), and NIKLSVQMKL (SEQ ID NO:7). Particularly preferred such segments include, for example, SVQMKL (SEQ ID NO:5), IKLSVQMKL (SEQ ID NO:6), and NIKLSVQMKL (SEQ ID NO:7).

In certain embodiments, segments of SEQ ID NO:2 or homologs thereof include at least one amino acid of SEQ ID NO:2 or homologs thereof, and preferably at least four amino acids of SEQ ID NO:2 or homologs thereof (preferably, contiguous amino acids). In certain preferred embodiments, segments of SEQ ID NO:2 include those in which deletions have been made at the C-terminus by 1, 2, 3, 4, 5, or 6 residues. Particularly preferred segments of SEQ ID NO:2 that can be used in forming the partial peptide mimetics of the present invention include I, IIVK (SEQ ID NO:3), and IIVKLN (SEQ ID NO:9).

The β-turn inducing scaffold can be a chemical scaffold, such as a dibenzofuran-containing scaffold or biphenyl-containing scaffold. Preferably, it is a dibenzofuran-containing scaffold. More preferably, the dibenzofuran-containing scaffold is that shown in the Examples Section (Scheme 1) and is referred to herein as "DBF." It should be understood that the length of the hydrocarbon chains off the phenyl rings in the scaffold and attached to the peptides can vary in length.

Such partial peptide mimetics are active with respect to a number of biological activities. This is exemplified by the data shown herein with respect to specific partial peptide mimetics composed of a β-sheet-inducing biphenylfuran scaffold and two short amino acid sequences from βpep-25. They can be as effective as βpep-25 at inhibiting endothelial cell proliferation and angiogenesis in vitro. For example, in a mouse xenograft model for ovarian carcinoma, two variations of the partial mimetic are observed to be slightly more effective than βpep-25 by reducing tumor volume by up to 85%. Immunohistochemical staining indicates that antitumor activity is mediated by significant reduction in vessel density and endothelial cell proliferation, as well as increased cell apoptosis. Overall, the partial peptide mimetic demonstrates improved bioavailability over βpep-25 and the potential for obtaining an orally active, small molecule of an angiogenesis inhibitory protein. Because of this anti-angiogenic behavior it is believed that such partial peptide mimetics can be used to inhibit pathologic disorders such as atherosclerosis, restenosis, diabetic retinopathy, neovascular glaucoma, rheumatoid arthritis, and endometriosis. This can be evaluated readily by one of skill in the art using appropriate in vitro and in vivo models.

Particularly preferred partial peptide mimetics include 6DBF1, 6DBF7, and 11DBF7, of which even more preferred are 6DBF7 and 11DBF7. The sequences of these DBF analogs (which are partial peptide mimetics) are shown in Table 1.

Such partial peptide mimetics can be in their free acid form or they can be amidated at the C-terminal carboxylate group. The present invention also includes homologs of the peptide sequences listed herein, which typically have structural similarity with such peptides. A "homolog" of a polypeptide includes one or more conservative amino acid substitutions, which are selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can generally be substituted for another amino acid without substantially altering the structure of a polypeptide.

For the purposes of this invention, conservative amino acid substitutions are defined to result from exchange of amino acids residues from within one of the following classes of residues: Class I: Ala, Gly, Ser, Thr, and Pro (representing small aliphatic side chains and hydroxyl group side chains); Class II: Cys, Ser, Thr, and Tyr (representing side chains including an —OH or —SH group); Class III: Glu, Asp, Asn, and Gln (carboxyl group containing side chains): Class IV: His, Arg, and Lys (representing basic side chains); and Class V: Ile, Val, Leu, Phe, Met, Phe, Trp, Tyr, and His (representing hydrophobic side chains). The classes also include related amino acids such as 3Hyp and 4Hyp in Class I; homocysteine in Class II; 2-aminoadipic acid, 2-aminopimelic acid, γ-carboxyglutamic acid, β-carboxyaspartic acid, and the corresponding amino acid amides in Class III; ornithine, homoarginine, N-methyl lysine, dimethyl lysine, trimethyl lysine, 2,3-diaminopropionic acid, 2,4-diaminobutyric acid, homoarginine, sarcosine and hydroxylysine in Class IV; substituted phenylalanines, norleucine, norvaline, 2-aminooctanoic acid, 2-aminoheptanoic acid, statine and β-valine in Class V; and naphthylalanines, substituted phenylalanines, tetrahydroisoquinoline-3-carboxylic acid, and halogenated tyrosines in Class V.

Polypeptide homologs, as that term is used herein, also include modified polypeptides. Modifications of polypeptides of the invention include chemical and/or enzymatic derivatizations at one or more constituent amino acid, including side chain modifications, backbone modifications, and N- and C-terminal modifications including acetylation, hydroxylation, methylation, amidation, and the attachment of carbohydrate or lipid moieties, cofactors, and the like.

Such homologs provide partial peptide mimetics with one or more of the biological activities described herein.

The partial peptide mimetics, particularly the peptide portions of the partial peptide mimetics of the invention, may be synthesized by the solid phase method using standard methods based on either t-butyloxycarbonyl (BOC) or 9-fluorenylmethoxy-carbonyl (FMOC) protecting groups. This methodology is described by G. B. Fields et al. in *Synthetic Peptides: A User's Guide*, W. M. Freeman & Company, New York, N.Y., pp. 77-183 (1992).

A preferred partial peptide mimetic is characterized by having at least one of the biological activities described herein. The biological activity of a polypeptide can be determined, for example, as described herein or by methods well known to one of skill in the art.

Compositions comprising one or more of the partial peptide mimetics of this invention with an optional carrier (e.g., a pharmaceutically acceptable carrier) can be added to cells in culture or used to treat patients, such as mammals. Where the partial peptide mimetics are used to treat a patient, the partial peptide mimetic is preferably combined in a pharmaceutical composition with a pharmaceutically acceptable carrier, such as a larger molecule to promote stability or a pharmaceutically acceptable buffer that serves as a carrier.

Treatment can be prophylactic or therapeutic. Thus, treatment can be initiated before, during, or after the development of the condition (e.g., bacterial infection or endotoxemia). As such, the phrases "inhibition of" or "effective to inhibit" a condition such as bacterial infection and/or endotoxemia, for example, includes both prophylactic and therapeutic treatment (i.e., prevention and/or reversal of the condition).

The partial peptide mimetics of the present invention can be administered alone or in a pharmaceutically acceptable buffer, as an antigen in association with another protein, such as an immunostimulatory protein or with a protein carrier such as, but not limited to, keyhole limpet hemocyanin (KLH), bovine serum albumin (BSA), ovalbumin, or the like.

Partial peptide mimetics can be conjugated to other proteins using standard methods such as activation of the carrier molecule with a heterobifunctional sulfosuccinimidyl 4-(n-maleimidomethyl) cyclohexane-1-carboxylate reagent. Cross-linking of an activated carrier to a peptide can occur by reaction of the maleimide group of the carrier with the sulflydryl group of a peptide containing a cysteine residue. Conjugates can be separated from nonconjugated molecules through the use of gel filtration column chromatography or other methods known in the art.

The partial peptide mimetics can be combined with a variety of physiological acceptable carriers for delivery to a patient including a variety of diluents or excipients known to those of ordinary skill in the art. For example, for parenteral administration, isotonic saline is preferred. For topical administration a cream, including a carrier such as dimethylsulfoxide (DMSO), or other agents typically found in topical creams that do not block or inhibit activity of the peptide, can be used. Other suitable carriers include, but are not limited to alcohol, phosphate buffered saline, and other balanced salt solutions.

The partial peptide mimetics of this invention that demonstrate biological activity can be administered in a variety of ways, including intravenously, topically, orally, and intramuscularly to a variety of mammals, including humans, mice and rabbits. The partial peptide mimetics can be administered as a single dose or in multiple doses. Preferably the dose is an effective amount as determine by the standard methods described herein and includes about 1 microgram to about 1,000 micrograms pretreatment, more preferably about 50 to about 250 micrograms pretreatment. Those skilled in the art of clinical trials will be able to optimize dosages of particular partial peptide mimetics through standard trial studies.

Preferred partial peptide mimetics are anti-angiogenic. Angiogenesis is crucial to numerous biological functions in the body, from normal processes like embryogenesis and wound healing to abnormal processes like tumor growth, arthritis, restenosis, atherosclerosis, diabetic retinopathy, neovascular glaucoma, and endometriosis. The use of agents that can inhibit angiogenesis in vitro and in vivo, particularly in anti-tumor research, has indicated that anti-angiogenic therapy will be a promising therapeutic modality in the future. The search for angiogenic inhibitors has been focused on controlling two of the processes that promote angiogenesis: endothelial cell (EC) growth and adhesion primarily because ECs are more accessible than are other cells to pharmacologic agents delivered via the blood and ECs are genetically stable and are not easily mutated into drug resistant variants. Most anti-angiogenic agents have been discovered by identifying endogenous molecules, primarily proteins, which inhibit EC growth. This traditional approach has produced a number of anti-angiogenics, such as platelet factor-4 (PF4), thrombospondin, tumor necrosis factor (TNF), interferon-γ inducible protein-10, angiostatin, endostatin, vasostatin, and bactericidal-permeability increasing (BPI) protein. In total, about forty anti-angiogenic agents, identified using various approaches, are currently known.

It has also been postulated that tumor growth can be controlled by deprivation of vascularization (Folkman J. Natl. Cancer. Inst., 82, 4-6 (1990); Folkman et al., J. Biol. Chem., 267, 10931-10934 (1992)). A growing number of endogenous inhibitors of angiogenesis such as platelet factor-4 (PF4), interferon-γ inducible protein-10 (IP-10), thrombospondin-1 (TSP-1), angiostatin, as well as synthetic agents, e.g., thalidomide, TNP-470, and metalloproteinase inhibitors have been described. Some of these agents are currently being tested in phase I/II clinical trials. Previous research described in Griffioen et al., Blood, 88, 667-673 (1996), and Griffioen et al., Cancer Res., 56, 1111-1117 (1996) has shown that pro-angiogenic factors in tumors induce down-regulation of adhesion molecules on endothelial cells in the tumor vasculature and induce anergy to inflammatory signals such as tumor necrosis factor α (TNF-α), interleukin-1, and interferon-γ. EC exposed to vascular endothelial cell growth factor (VEGF) (Griffioen et al., Blood, 88, 667-673 (1996)) and basic fibroblast growth factor (bFGF) (Griffioen et al., Blood, 88, 667-673 (1996); and Melder et al., Nature Med, 2, 992-997 (1996)) have a severely hampered up-regulation of intercellular adhesion molecule-1 (ICAM-1) and induction of vascular cell adhesion molecule-1 (VCAM-1) and E-selectin. This phenomenon, which was named tumor-induced EC anergy, is one way in which tumors with an angiogenic phenotype may escape infiltration by cytotoxic leukocytes.

Because angiogenesis-mediated down-regulation of endothelial adhesion molecules (EAM) may promote tumor outgrowh by avoiding the immune response (Griffloen et al., Blood, 88, 667-673 (1996); Kitayama et al., Cancer. Res., 54 4729-4733 (1994); and Piali et al., J. Exp. Med, 181, 811-816 (1995)), it is believed that inhibition of angiogenesis would overcome the down-regulation of adhesion molecules and the unresponsiveness to inflammatory signals. In support of this hypothesis, a relation between E-selectin up-regulation and the angiostatic agent AGM-1470 has been reported (Budson et al., Biochem. Biophys. Res. Comm., 225, 141-145 (1996)). It has also been shown that inhibition of angiogenesis by PF-4 up-regulates ICAM-1 on bFGF-simulated EC. In addition, inhibition of angiogenesis by PF4 overcomes the angiogenesis-associated EC anergy to inflammatory signals.

Thus, the present invention provides a method for inhibiting endothelial cell proliferation in a patient (e.g., a mammal such as a human). This involves administering to a patient an amount of a composition (typically a pharmaceutical composition) effective to inhibit the growth or endothelial cells, wherein the composition includes one or more partial peptide mimetics described herein. Analogously, the present invention provides a method for inhibiting endothelial cell proliferation in vitro (e.g., in a cell culture). This method involves contacting cells with an amount of a composition effective to prevent and/or reduce the growth of endothelial cells, wherein the composition includes one or more partial peptide mimetics described herein.

For determining the amount of endothelial cell proliferation in vivo, various methods known to one of skill in the art could be used. For example, for evaluation of endothelial cell growth in tumors, tissue sections can be appropriately stained to quantify vessel density. For determining the amount of endothelial cell proliferation in vitro, an EC Proliferation Assay can be used that involves the uptake of tritiated thymidine by cells in cell culture. A partial peptide mimetic that is "active" for inhibiting endothelial cell proliferation is preferably one that causes an at least 10% reduction in endothelial cell proliferation at a concentration lower than $10^{-4}$ M. Alternatively, inhibition of endothelial cell proliferation for an "active" partial peptide mimetic in vitro is preferably at an IC50 level of less than 80 µM (more preferably less than 50 µM, and even more preferably less than 25 µM) as determined using the assay described in the Examples Section.

The present invention also provides a method for inhibiting angiogenic-factor mediated inter-cellular adhesion molecule (ICAM) expression down-regulation (and/or promoting ICAM expression) in a patient (e.g., a mammal such as a human). This involves administering to a patient an amount of a composition effective to prevent and/or reduce the amount of ICAM expression down-regulation, wherein the composition includes one or more partial peptide mimetics described herein. Analogously, the present invention provides a method for inhibiting angiogenic-factor mediated intercellular adhesion molecule expression down-regulation (and/or promoting ICAM expression) in vitro (e.g., in a cell culture). This method involves contacting cells with an amount of a composition effective to prevent and/or reduce the amount of ICAM expression down-regulation, wherein the composition includes one or more partial peptide mimetics described herein.

The present invention provides a method for inhibiting angiogenesis (i.e., new blood vessel formation) in a patient (e.g., a mammal such as a human). This involves administering to a patient an amount of a composition effective to prevent and/or reduce angiogenesis, wherein the composition includes one or more partial peptide mimetics described herein. Analogously, the present invention provides a method for inhibiting angiogenesis in vitro (e.g., in a cell culture). This method involves contacting cells with an amount of a composition effective to prevent and/or reduce angiogenesis, wherein the composition includes one or more partial peptide mimetics described herein.

For determining the amount of angiogenesis in vivo, various methods known to one of skill in the art could be used. For example, for evaluation of angiogenesis in tumors, tissue sections can be appropriately stained to quantify vessel density. For determining the amount of angiogenesis in vitro, an Angiogenesis Assay can be used that involves the disappearance of EC sprouting in cell culture. A polypeptide that is "active" for angiogenesis inhibition is preferably one that causes an at least 10% reduction in endothelial cell sprouting at a concentration lower than $10^{-4}$ M. Alternatively, inhibition of angiogenesis for a partial peptide mimetic in vitro is preferably at a level of less than 85% sprouting (more preferably less than 75% sprouting, even more preferably 50% sprouting, and even more preferably less than 35%) as determined using the collagen gel-based assay described in the Examples Section.

Similarly, such anti-angiogenic compositions can be used to control pathologic disorders such as atherosclerosis, restenosis, diabetic retinopathy, neovascular glaucoma, rheumatoid arthritis, and endometriosis. This can be demonstrated using standard techniques and models known to one of skill in the art.

The present invention provides a method for inhibiting tumorigenesis in a patient (e.g., a mammal such as a human). This involves administering to a patient an amount of a composition effective to prevent and/or reduce tumor growth, wherein the composition includes one or more partial peptide mimetics described herein. Methods of determining the inhibition of tumorigenesis are well known to those of skill in the art, including evaluation of tumor shrinkage, survival, etc.

The present invention provides a method for treating bacterial infection and/or endotoxemia in a patient (e.g., a mammal such as a human). This involves administering to a patient an amount of a composition effective to inhibit the bacterial infection and/or to neutralize endotoxin, wherein the pharmaceutical composition includes one or more partial peptide mimetics described herein. Analogously, the present invention provides a method for inhibiting bacterial infection and/or endotoxemia in vitro (e.g., in a cell culture). This method involves contacting cells with an amount of a composition effective to inhibit the bacterial infection and/or to neutralize endotoxin, wherein the composition includes one or more partial peptide mimetics described herein.

In both the in vivo and in vitro methods, "inhibiting" a bacterial infection includes preventing as well as reversing or reducing the growth of bacteria in a patient or a cellular sample, and "neutralizing" endotoxin includes binding LPS and thereby removing it from the system of a patient or a cellular sample. The level of bacterial infection can be determined according to known bactericidal assays. The level of endotoxemia can be determined according to known LPS neutralization assays. These assays can be used to determine the effectiveness of a polypeptide, whether used in vivo or in vitro. To determine the effectiveness of the treatment of a patient having a bacterial infection, a blood sample can be taken, a culture developed, and the amount of live bacteria determined. To determine the effectiveness of the treatment of a patient having endotoxemia, a blood sample can be taken, a culture developed, and the amount of cytokines (e.g., TNF-α, IL-1) can be determined using methods known to one of skill in the art. For example, the WEHI assay can be used for the detection of TNF-α (Battafarano et al., *Surgery* 118, 318-324 (1995)).

The effective amount of a partial peptide mimetic of the present invention will depend on the condition being treated and on the desired result. For example, treating a bacterial infection will depend on the bacterial infection, the location of the infection, and the partial peptide mimetic. An effective amount of the partial peptide mimetic for treating bacterial infection is that amount that diminishes the number of bacteria in the animal and that diminishes the symptoms associated with bacterial infection such as fever, pain, and other associated symptoms of the bacterial infection. The effective amount of a peptide can be determined by standard dose response methods.

Alternatively, an effective amount of a partial peptide mimetic for treating a bacterial infection can be determined in an animal system such as a mouse. Acute peritonitis can be induced in mice such as outbred Swiss webster mice by intraperitoneal injection with bacteria such as *P. aeruginosa* as described by Dunn et al. (*Surgery*, 98:283, 1985); Cody et al. (*Int. Surg. Res.*, 52:315, 1992). Bactericidal activity can be evaluated against a variety of bacteria, preferably Gram-negative bacteria, but the types of bacteria can include *Pseudomonas* spp including *P. aeruginosa* and *P. cepacia*, *E. coli* strains, including *E. coli* B, *Salmonella*, *Proteus mirabilis* and *Staphylococcus* strains such as *Staphylococcus aureus*. Partial peptide mimetics with endotoxin neutralizing activity can be used to treat mammals infected with Gram-negative bacteria systemically and that exhibit symptoms of endotoxin shock such as fever, shock, and TNF-α release.

Endotoxin neutralizing activity can be measured by determining the molar concentration at which the peptide completely inhibits the action of lipopolysaccbaride in an assay such as the Limulus amoebocyte lysate assay (LAL, Sigma Chemicals, St. Louis, Mo.) or the chromogenic LAL 1000 test (Biowhittacker, Walkersville, Md.). Endotoxin neutralizing activity can also be measured by calculating an inhibitory dose 50 ($LD_{50}$) using standard dose response methods. An inhibitory dose 50 is that amount of peptide that can inhibit 50% of the activity of endotoxin.

The present invention also provides a method for inhibiting the amount of TNF-α in a patient (e.g., a mammal such as a human). This involves administering to a patient an amount of a composition effective to inhibit the amount of TNF-α in a patient's system as determined by evaluating serum levels of TNF-α, wherein the composition includes one or more partial peptide mimetics described herein. Analogously, the present invention provides a method for inhibiting the amount of TNF-α in vitro (e.g., in a cell culture). This method involves incubating cells with an amount of a composition effective to decrease TNF-α amounts in the cell culture, wherein the composition includes one or more partial peptide mimetics described herein. For both in vivo and in vitro methods, the WEHI assay can be used for the detection of TNF-a (Battafarano et al., *Surgery*, 118, 318-324 (1995)) in cell culture or in serum from a patient. Alternatively, the amount of TNF-α in a sample can be assayed using an anti-TNF-α antibody. A partial peptide mimetic "active" for decreasing TNF-α can be evaluated using an in vitro test, and preferably shows an at least 10% decrease in the amount of TNF-α.

The invention will be further described by reference to the following detailed examples. These examples are offered to further illustrate the various specific and preferred embodiments and techniques. It should be understood, however, that many variations and modifications may be made while remaining within the scope of the present invention.

EXAMPLES

Experimental Protocol

Peptide Synthesis.

Peptides were synthesized using a Milligen/Biosearch 9600 peptide solid-phase synthesizer using fluorenyl-methoxycarbonyl chemistry. Lyophilized crude peptides were purified by preparative reversed-phase HPLC on a C18 column with an elution gradient of 0-60% acetonitrile with 0.1% trifluoroacetic acid in water. The purity and composition of the peptides were verified by HPLC (Beckman Model 6300) analysis of amino acid composition of hydrolysates prepared by treating the peptides under argon in 6 Normal (6 N) HCl for 24 hours at 110° C. The amino acid sequences of peptides were confirmed by N-terminal sequencing and mass spectrometry.

Synthesis of DBF Analogs.

Unexceptional phases of solid-phase peptide synthesis (SPPS) were carried out on a Milligen/Biosearch 9600 peptide synthesizer using fluorenylmethoxy-carbonyl (Fmoc) methodology and BOP/HOBT as coupling reagents. Fmoc-DBF-CO$_2$H (1) was prepared by slight modification of the reported method (H. Bekele et al., *J. Org. Chem.*, 62, 2259-2262 (1997).). In this nine-step synthesis, the intermediates and final product were characterized by TLC and $^1$H NMR, with GC-LRMS, $^{13}$C NMR, melting points (mp), and IR being used as appropriate. Coupling of 1 to I$_{20}$ (isoleucine at residue 20 of the βpep-25 sequence) as well as of L$_{11}$ (leucine at residue 11 of the βpep-25 sequence) to the peptide-DBF-NH$_2$ was performed on the synthesizer. Coupling of Fmoc-K$_{10}$-CO$_2$H (wherein K$_{10}$ refers to the lysine at residue 10 of the βpep-25 sequence) to the peptide-DBF-L$_{11}$-NH$_2$ sequence was difficult and required manual SPPS using the more reactive HATU reagent (L. A. Carpino, *J. Am. Chem. Soc.*, 115, 4397-4398 (1993)).

The remaining chemical couplings used for production of the DBF analogs listed in Table 1 were carried out using BOP/HOBT conditions on the peptide synthesizer. After the final Fmoc deprotection, each of the DBF peptide analogs (partial peptide mimetics) was released from the resin with simultaneous removal of all acidolyzable trityl and tert-butyl side-chain protecting groups using Reagent K (D. S. King et al., *Int. J. Pept. Protein. Res.*, 36, 255-266 (1990)). A Rink amide or similar resin was used to provide the primary amide form of the C-terminal D24 unit. Lyophilized crude peptides were purified by preparative reversed-phase HPLC on a C18 column using a Hewlett-Packard 1090 system. An elution gradient of 0-60% acetonitrile in water (0.1% trifluoroacetic acid) was used. The purity and composition of the peptides was verified by analytical HPLC, matrix assisted laser desorption ionization (MALDI) mass spectrometry using a Hewlett-Packard G2025A system and sinapinic acid as matrix, and analysis of amino acid composition of hydrolysates (6N HCl, 110° C., 24 hours (h), under argon).

NMR Spectroscopy.

For NMR measurements, freeze-dried DBF analogs were dissolved in water-DMSO-DPC mixture. Peptide concentration was 3 mM. pH was adjusted to pH 5.7 by adding μL quantities of NaOD or HCl to the peptide sample. NMR spectra were acquired on a Varian UNITY Plus-600 NMR spectrometer.

2D-homonuclear TOCSY with DIPSI (M. Piotto et al., *J. Biomol. NMR*, 2, 661-665 (1992)) spinlock (mixing time 80 milliseconds (ms)) was used to identify spin systems. 2D NOESY experiments (G. Wider et al., *J. Magn. Reson.*, 56, 207-234 (1985)) were performed for sequential assignments and conformational analysis. WATERGATE (A. J. Shaka et al., *J. Magn. Reson.*, 77, 274-293 (1988); and S. P. Rucker et al., *Mol. Phys.*, 68, 509-517 (1989)) was used to attenuate the water resonance. All spectra were collected at 25° C. as 256 to 512 t1 experiments, each with 2048 complex data points over a spectral width of 6 kHz in both dimensions with the carrier placed on the water resonance. Sixteen scans were time averaged per t1 experiment. Data were processed directly on the spectrometer using VNMR (Varian, Inc., Palo Alto) or NMRPipe (F. Delaglio et al., *J. Biomol. NMR*, 6,277-293 (1995)) on an SGI workstation.

Structural Modeling.

Analysis of NOE growth curves indicated that backbone to backbone inter-proton NOEs were normally maximum at about 200 ms. Interproton distance constraints were derived from NOEs assigned in $^1$H NOESY spectra acquired with mixing times of 100 ms. NOEs were classified as strong, medium, weak, or very weak corresponding to upper bound distance constraints of 2.8, 3.3, 4.0, and 4.5 Å, respectively. The lower bound restraint between non-bonded protons was set to 1.8 Å. Pseudo-atom corrections were added to the upper bound distance constraints where appropriate, and a 0.5 Å correction was added to the upper bound for NOEs involving methyl protons. Hydrogen bond constraints were identified from the pattern of sequential and interstrand NOEs involving NH and CaH protons, together with evidence of slow amide proton-solvent exchange. Each hydrogen bond identified was defined using two distance constraints; $r_{NH-O}$=1.8 to 2.5 Å, and rN—O=1.8 to 2.5 Å.

Derived internuclear distance constraints were used in calculating structures for 6DBF7 by using X-PLOR (A. T. Brunger, *X-plor Manual*, Yale University Press, New Haven (1992)). The molecule was created using parallhdg.pro force fields. A template coordinate set was generated by using the Template routine. The ab initio simulated annealing (SA) protocol was then used. The SA procedure ran high temperature dynamics (3000 K for 120 picoseconds (ps)) and then cooled down to 100 K in 50 K steps with 1.5 ps molecular dynamics at each step. Powell minimization was performed at 100 K for 1000 steps. Structure refinement was done based on simulated annealing starting at 1000 K and ending at 100 K. Final structures were subjected to the X-PLOR Accept routine with the violation threshold for NOEs of 0.5 Å and dihedral angles of 5°. Angles, bond lengths or impropers were not allowed to deviate from ideal geometry more than 5°, 0.05 Å and 5°, respectively. Structures were superimposed using the BIOSYM INSIGHT viewer (Molecular Simulations, Inc.) and were analyzed using X-PLOR analysis routines.

Cells, Cultures, and Reagents.

Human umbilical vein derived EC (HUVEC) were harvested from normal human umbilical cords by perfusion with 0.125% trypsin/EDTA. Harvested HUVECs were cultured in gelatin coated tissue culture flasks and subcultured 1:3 once a week in culture medium (RPMI-1640 with 20% human serum (HS), supplemented with 2 mM glutamine and 100 U/ml penicillin and 0.1 mg/ml streptomycin). Bovine capillary EC (BCE) were kindly provided by Dr. M. Furie (State University of New York, Stony Brook, USA) and were cultured in fibronectin coated tissue culture flasks in RPMI-1640 medium containing 10% FCS, glutamine and antibiotics.

EC Proliferation Measurement.

EC proliferation was measured using a [$^3$H]-thymidine incorporation assay. Proliferation of bFGF-stimulated (10 nanogram per milliliter (ng/ml)) human umbilical vascular EC (HUVEC) cultures was measured by quantification of $^3$H-thymidine incorporation. Proliferation is expressed as mean counts per minute (cpm) of quadruplicate cultures in three independent experiments (±SEM). EC were seeded at 5000 cells/well in flat-bottomed tissue culture plates and grown for 3 days in the absence or presence of regulators, in culture medium. During the last 6 hours of the assay, the culture was pulsed with 0.5 µCi [methyl-$^3$H]-thymidine/well. Human umbilical vein derived EC (HUVEC) were harvested from normal human umbilical cords by perfusion with 0.125% trypsin/EDTA. Harvested HUVECs were cultured in gelatin coated tissue culture flasks and subcultured 1:3 once a week in culture medium (RPMI-1640 with 20% human serum (HS), supplemented with 2 mM glutamine and 100 U/ml penicillin and 0.1 mg/ml streptomycin).

In Vitro Angiogenesis Assay.

Sprouting and tube formation of bovine EC (BCE) were studied using cytodex-3 beads overgrown with BCE in a 3-dimensional collagen gel (vitrogen-100, Collagen Corp., Fremont, Calif., USA) as described in D. Van der Schaft et al., *Blood*, 96,176-181 (2000). Following gelation, culture medium containing 20 ng/mL bFGF, with or without βpep-25 or DBF analogs, was applied on top of the gel. After 24 hours of cell culture at 37° C., photographs were made (not shown). The amount of sprouting in each well (i.e., the total length of the sprouts) was quantified by the computer program NIH image. To quantify differences in sprouting and tube formation, statistical analysis was performed using the Mann-Whitney U test. Using these data the $IC_{50}$ on EC proliferation and tube formation were quantified and are listed in Table 1.

Tumor Model Studies.

In all studies, female athymic nude mice (nu/nu, 5-6 weeks old) were used. These mice were purchased from the National Cancer Institute and allowed to acclimatize to local conditions for at least one week. Animals were given water and standard chow ad libitum, and were kept on a 12-hour light/dark cycle. All experiments were approved by the University of Minnesota Research Animal Resources ethical committee. Mice were randomized and split into three groups: 1) human serum albumin (10 mg/kg/day), 2) βpep-25 (10 mg/kg/day) and 3) DBF analog (10 mg/kg/day). Compounds were diluted in 100 mM SDS and administered using osmotic mini-pumps (Durect, Cupertino, Calif.). Exponentially growing MA148 human ovarian carcinoma cells, kindly provided by Prof. Ramakrishnan (R. P. Dings et al., *Cancer Res.*, 63, 382-385 (2003)) were cultured in RPMI 1640 medium (Life Technologies, Grand Island, N.Y.). This medium was supplemented with 10% fetal bovine serum and 1% penicillin/streptomycin (Cellgro, Mediatech, Washington, D.C.) at 37° C. and 5% $CO_2$. One hundred microliters (100 µL) of this tumor cell suspension ($2 \times 10^7$ cells/ml) was then injected subcutaneously into the right flank of each mouse. Pumps were implanted into the left flank of mice for subcutaneous administration of compound over a 28-day treatment span.

Two variants of this model were used: prevention and intervention. For the prevention variant, treatment was initiated at the time of inoculation with MA148 cells. For the intervention variant, tumors were allowed to grow to an average size of 50 mm$^3$ (usually day 7 post inoculation) before treatment was initiated. With either variant, animals were randomized prior to the initiation of treatment. Treatment was administered via osmotic mini-pumps (Durect, Cupertino, Calif.), which were implanted subcutaneously in the left flank of mice. Concentrated solutions of βpep-25 or DBF analogs were formulated such that the 28-day treatment period would be covered by implantation of a single pump. In each study, control groups of animals were administered either PBS or PBS containing human serum albumin. Tumor growth curves were found to be virtually identical in either of these control cases.

Tumor volume was determined by measuring the diameters of tumors using calipers (Scienceware, Pequannock, N.J.) using the equation for the volume of a spheroid: $(a^2 \times b \times \pi)/6$, where 'a' is the width and 'b' the length of the tumor. Measurements were performed two or three times per week. At the conclusion of an experiment, tumor weights were also taken following excision of the tumors from euthanized animals. Tumor weights correlated well with tumor volumes calculated in this way.

Immunohistochemistry.

Immunohistochemistry was used to assess microvessel density and the extent of total cell apoptosis. Tumor tissue was embedded in tissue freezing medium (Miles Inc, Elkart, Ind.) and shock frozen in liquid nitrogen. Ten millimeter (10 mm) thick sections of tissue were prepared for immunohistochemical analysis. For this, tissue sections were brought to room temperature, air dried overnight, and then fixed in acetone for 10 minutes. Slides were allowed to air dry for at least 30 minutes and were washed three times for 5 minutes each in phosphate-buffered saline (PBS, pH 7.4). Samples were then blocked with PBS containing 0.1% bovine serum albumin and 3% human serum albumin for at least 30 minutes at room temperature in a humidified box. Samples were subsequently incubated with phycoerytrin (PE)-conjugated monoclonal antibody to CD31 (PECAM-1) in a 1:50 dilution (Pharmigen, San Diego, Calif.) to stain for microvessel density. After 1-hour incubation at room temperature, slides were washed with PBS and immediately imaged using an Olympus BX-60 fluorescence microscope at 200× magnification.

To assess the extent of total cell apoptosis, tissue sections were stained by using the TUNEL (terminal deoxyribonucleotidyl transferase-mediated dUTP-nick-end labeling) assay, which was performed according to the manufacturer's instructions (in situ cell death detection kit, fluorescein; TUNEL, Roche). Digital images were stored and processed using Adobe Photoshop (Adobe Inc., Mountain View Calif.).

Quantification of microvessel density, the rate of proliferation and total cell apoptosis were determined as described earlier (R. Wild et al., *Microvasc. Res.*, 59, 368-376 (2000)). Statistical analysis was performed using the Student's t test.

Toxicity Assays.

As an indirect measurement of general toxicity, body weights of mice were monitored twice weekly, using a digital balance (Ohaus Florham, N.J.). To determine hematocrit and creatinine levels, blood samples were extracted by tail vein bleedings one day after terminating treatment and blood was collected in heparinized micro-bematocrit capillary tubes (Fisher; Pittsburgh, Pa.). For hematocrit levels, samples were spun down for 10 minutes in a micro-hematocrit centrifuge (Clay-Adams; NY), and the amount of hematocrit was determined using an international microcapillary reader (IEC; Needham, Mass.). To obtain creatinine levels, a kit was purchased from Sigma (Sigma Diagnostics; St Louis, Mo.) and used according to the manufacturer's instructions.

Results and Discussion

Detailed Structure-Activity Evaluation.

For input into designing the partial peptide mimetics of the present invention, a complete structure-activity analysis with βpep-25 was performed. Working with this relatively small peptide allowed for a thorough assessment of desirable residues using alanine scanning and walk-through variants.

Dodecapeptide walk-through variants that walk through the βpep-25 sequence, shifting three residues in each peptide were prepared and are listed in FIG. 1A. Their effect on EC proliferation is also indicated in FIG. 1A with IC50 values. Only three walk-through peptides demonstrated any significant anti-proliferative activity relative to βpep-25, and, as with results from alanine scanning, these peptides also encompass β-strands 1 and 2. Based on these results, it can be concluded that activity is localized within β-strands 1 and 2. For orientation, the β-strand alignment for βpep-25 is depicted in FIG. 1B, with key sequences being boxed-in.

Residues that demonstrated the most significant drop in the ability of βpep-25 to inihibit EC proliferation are hydrophobic residues within the first two β-strands: $I_3$, $L_5$, $V_7$, $L_{11}$, and $I_{20}$ (these refer to the specific amino acid residues at the position indicated by the subscript in βpep-25). Conformationally, these hydrophobic residues lie on the same face of the amphipathic anti-parallel β-sheet.

Using these structure-activity relationships, a series of new molecules were designed. In these, the β-strand 3 and turn 2 of βpep-25 were omitted and a dibenzofuran (DBF) β-turn mimetic (H. Diaz et al., *J. Am. Chem. Soc.*, 115, 3790-3791 (1993); and K. Y. Tsang et al., *J. Am. Chem. Soc.*, 116, 3988-4005 (1994)) was used in place of turn 1 and the remainder of β-strand 1 (residues 1-11 of β-pep-25 or SEQ ID NO:1) and β-strand 2 (residues 20-26 of βpep-25 or SEQ ID NO:1). The DBF β-turn mimetic was used in order to maintain the bioactive β-sheet conformation of βpep-25.

A number of β-turn inducing scaffolds are known. The dibenzofuran scaffold developed by Kelly et al. (H. Diaz et al., *J. Am. Chem. Soc.*, 115, 3790-3791 (1993); and K. Y. Tsang et al., J. Am. Chem. Soc., 116, 39884005 (1994)) is an α, ω-amino acid that has been incorporated into peptides of varying length by both the Kelly group and others. Notably, replacement of two, β-turn-inducing, natural amino acids in the protein scyllatoxin (a 31-mer) by the DBF scaffold provided an analog whose secondary structure and activity were indistinguishable from the parent toxin. Kelly has demonstrated that when the DBF unit is inserted between a pair of lipophilic amino acid residues, a "hydrophobic cluster" is created wherein the sidechains of those residues are nested within the hydrophobic pocket created by the aromatic rings of the canted DBF subunit. Because of the desire to design peptide analogs of relatively small size, DBF is an excellent choice since it could be inserted between residues $I_{20}$ and $L_{11}$ of βpep-25. The lypophilic isoleucine at residue 20 is one of the important, hydrophobic residues associated with βpep-25 anti-angiogenic activity.

The Fmoc-protected version of the Kelly DBF is shown below in Scheme 1 with several subtle improvements made in the synthesis (bolded conditions).

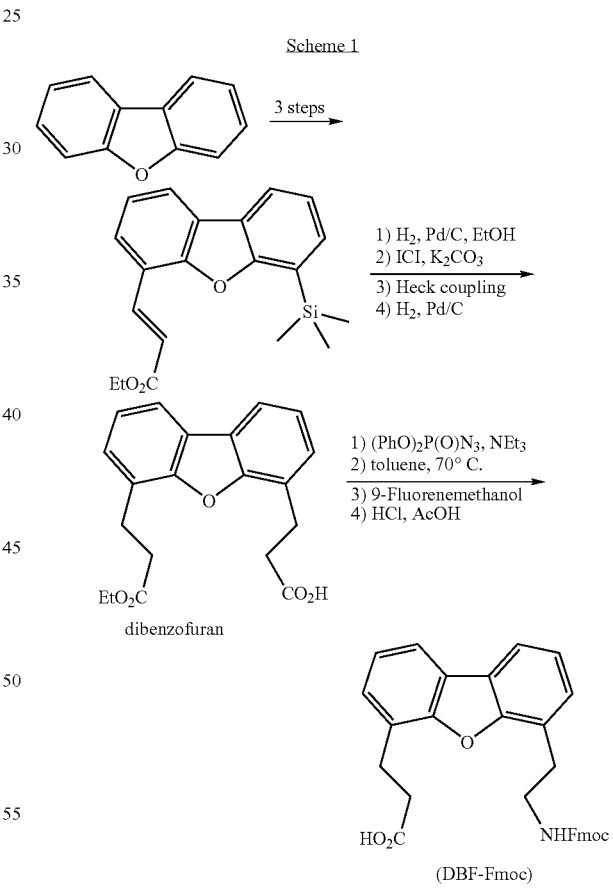

Scheme 1

The parent DBF-based compound depicted in FIG. 1C is called 11DBF7, where numbers at the left and right of DBF refer to the number of amino acid residues in the N- and C-terminal strands from βpep-25, respectively, with the DBF turn mimic replacing amino acid residues 12-19 of βpep-25, SEQ ID NO:1. To identify the shortest sequences required for bioactivity, a series of N- and C-terminal deletion variants of 11DBF7 were made as listed in Table 1.

In the provisional application to which this application claims priority, some of these were referred to as CF-1 through CF-8. Furthermore, in the provisional application to which this application claims priority, the segments of SEQ ID NO:1 were written in reverse order (i.e., from the C-terminus to the N-terminus), which upon reading the context of the provisional application would be clear to one of skill in the art. For example, CF-1 was written as DN[25]LKVII[DBF]L, wherein the N[25] indicates the asparagine is residue 25 of βpep-25 or SEQ ID NO:1.

Figure 2:
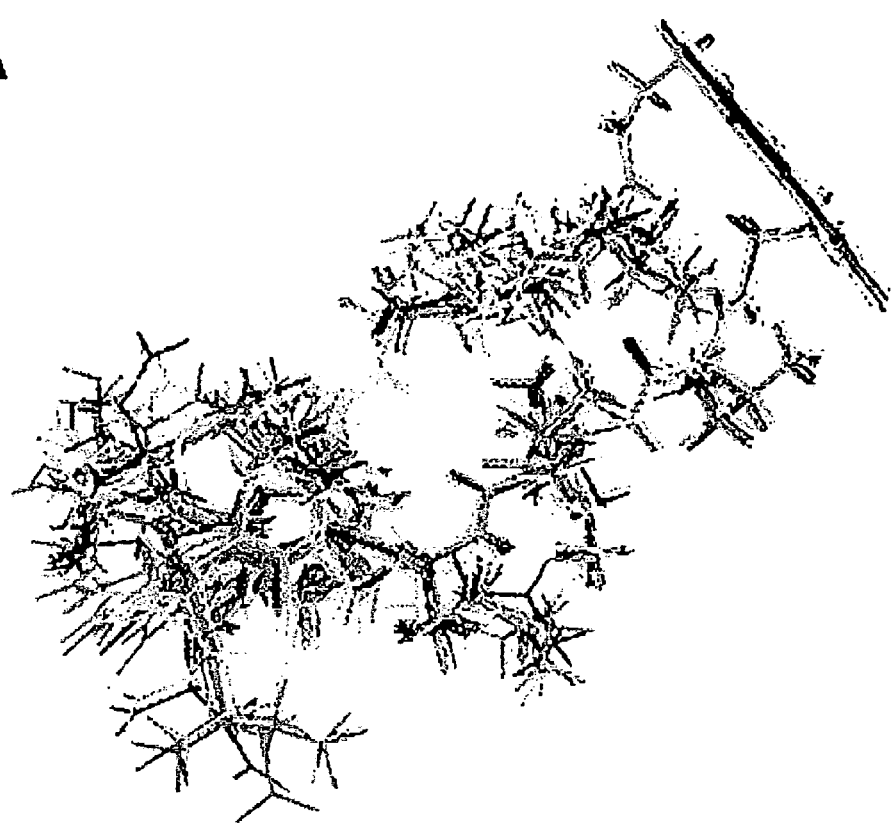
FIG. 2. The superposition of 6DBF7 derived from NMR analysis is shown in FIG. 2(A), with the chemical 3D structure illustrated in FIG. 2(B).
Figure 2:
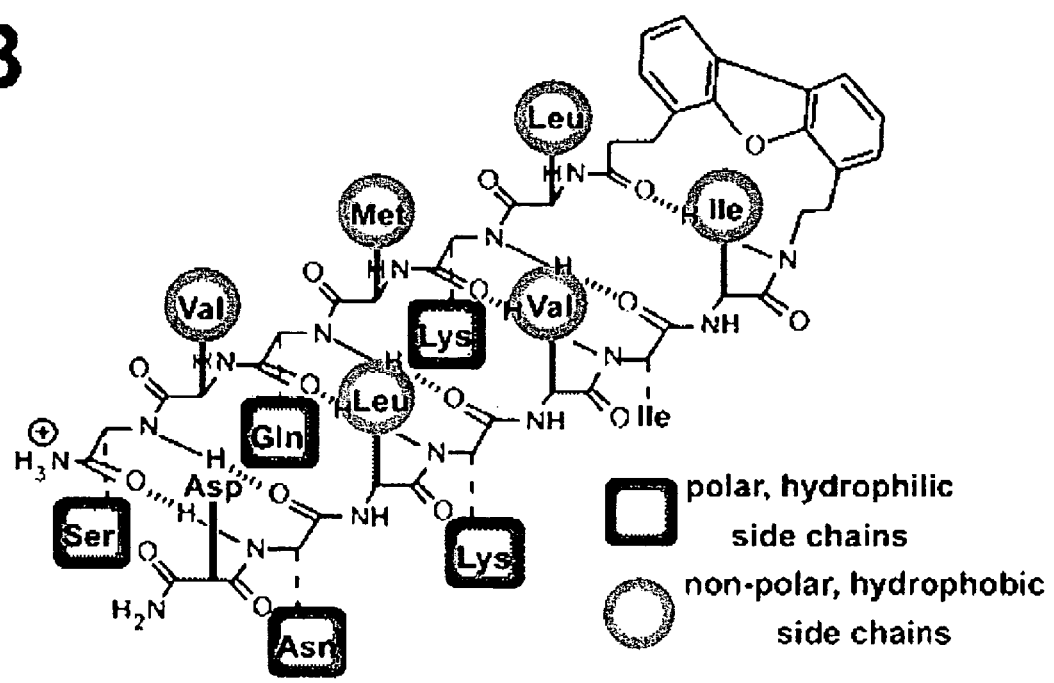

Superposition of the resulting 28 structures is shown in FIG. 2A, along with a simplified illustration of this folding pattern in FIG. 2B, which highlights residues on both hydrophobic and hydrophilic surfaces of the β-sheet. Notice in this structure that the two aliphatic hydrophobic residues Leu and Ile in 6DBF7 are packed against the phenyls of the DBF group. In effect, this sets up and helps stabilize the β-sheet fold. Based on this structural information on 6DBF7, it can be concluded that other DBF analogs would fold similarly,

TABLE 1

N- and C-terminal Deletion Variants of 11DBF7 and Angiostatic Potential.

| Compound | Amino Acid Sequence | EC Proliferation (IC50) | | % Sprouting |
|---|---|---|---|---|
| | | IC50 | % Inhibition at 25 μM | |
| β-pep-25 (parent) | ANIKLSVQMKLFKRHLKWKIIVKLNDGRELSLD (SEQ ID NO: 1) | 3 μM | 90% | 8 ± 5%* |
| DBF Analogs | | | | |
| 11DBF7 (CF-8) | ANIKLSVQMKL-[DBF]-IIVKLND (SEQ ID NO: 8)-[DBF]-(SEQ ID NO: 2) | 12 μM | 92% | 23 ± 10%* |
| 10DBF7 (CF-7) | NIKLSVQMKL-[DBF]-IIVKLND (SEQ ID NO: 7)-[DBF]-(SEQ ID NO: 2) | 12 μM | 69% | 57 ± 17.5%* |
| 9DBF7 (CF-6) | IKLSVQMKL-[DBF]-IIVKLND (SEQ ID NO: 6)-[DBF]-(SEQ ID NO: 2) | 20 μM | 57% | 76 ± 40%* |
| 6DBF7 (CF-4) | SVQMKL-[DBF]-IIVKLND (SEQ ID NO: 5)-[DBF]-(SEQ ID NO: 2) | 15 μM | 68% | 60 ± 12%* |
| 4DBF7 (CF-3) | QMKL-[DBF]-IIVKLND (SEQ ID NO: 4)-[DBF]-(SEQ ID NO: 2) | 25 μM | 46% | 99 ± 5% |
| 3DBF7 (CF-2) | MKL-[DBF]-IIVKLND [DBF]-(SEQ ID NO: 2) | —[a] | 0% | 84 ± 30% |
| 1DBF7 (CF-1) | L-[DBF]-IIVKLND [DBF]-(SEQ ID NO: 2) | — | 0% | — |
| 11DBF6 | ANIKLSVQMKL-[DBF]-IIVKLN (SEQ ID NO: 8)-[DBF]-(SEQ ID NO: 9) | 22 μM | | ND |
| 11DBF4 | ANIKLSVQMKL-[DBF]-IIVK (SEQ ID NO: 8)-[DBF]-(SEQ ID NO: 3) | 35 μM | | ND |
| 11DBF1 | ANIKLSVQMKL-[DBF]-I (SEQ ID NO: 8)-[DBF] | 23 ± 5 μM | | ND |
| 6DBF6 | SVQMKL-[DBF]-IIVKLN (SEQ ID NO: 5)-[DBF]-(SEQ ID NO: 9) | 42 μM | | ND |
| 6DBF4 | SVQMKL-[DBF]-IIVK (SEQ ID NO: 5)-[DBF]-(SEQ ID NO: 3) | — | | ND |
| 6DBF3 | SVQMKL-[DBF]-IIV (SEQ ID NO: 5)-[DBF] | — | | ND |
| 6DBF2 | SVQMKL-[DBF]-II (SEQ ID NO: 5)-[DBF] | — | | ND |
| 6DBF1 | SVQMKL-[DBF]-I (SEQ ID NO: 5)-[DBF] | 76.1 ± 10.9 μM | | ND |

*Significant inhibition (p < 0.03; Mann-Whitney U test).
[a]No effect on the assay;
ND = Not Done.

β-Sheet Structure is Preserved in DBF Analogs.

NMR spectroscopy was used to investigate whether β-sheet conformation was preserved in DBF analogs. Analogs 11DBF7 and 6DBF7 that have more equivalent β-strand lengths, were the focus of this structural study. Due to limited water solubility and the desire to mimic a membrane-like environment, these compounds were investigated in dodecylphosphocholine (DPC) micelles. At the millimolar concentrations required for NMR work, 11DBF7 gave overlapping resonances that made spectral analysis ambiguous. 6DBF7 gave excellent NMR spectra that allowed complete structure analysis. NOEs and coupling constants diagnostic of anti-parallel β-sheet conformation were readily identified and used in computational modeling.

albeit to various extents depending on the lengths of the two strands, i.e., strands of equal length are expected to be better able to form β-sheets.

DBF Analogs Inhibit EC Proliferation and Retain Anti-Angiogenic Activity.

Figure 3:
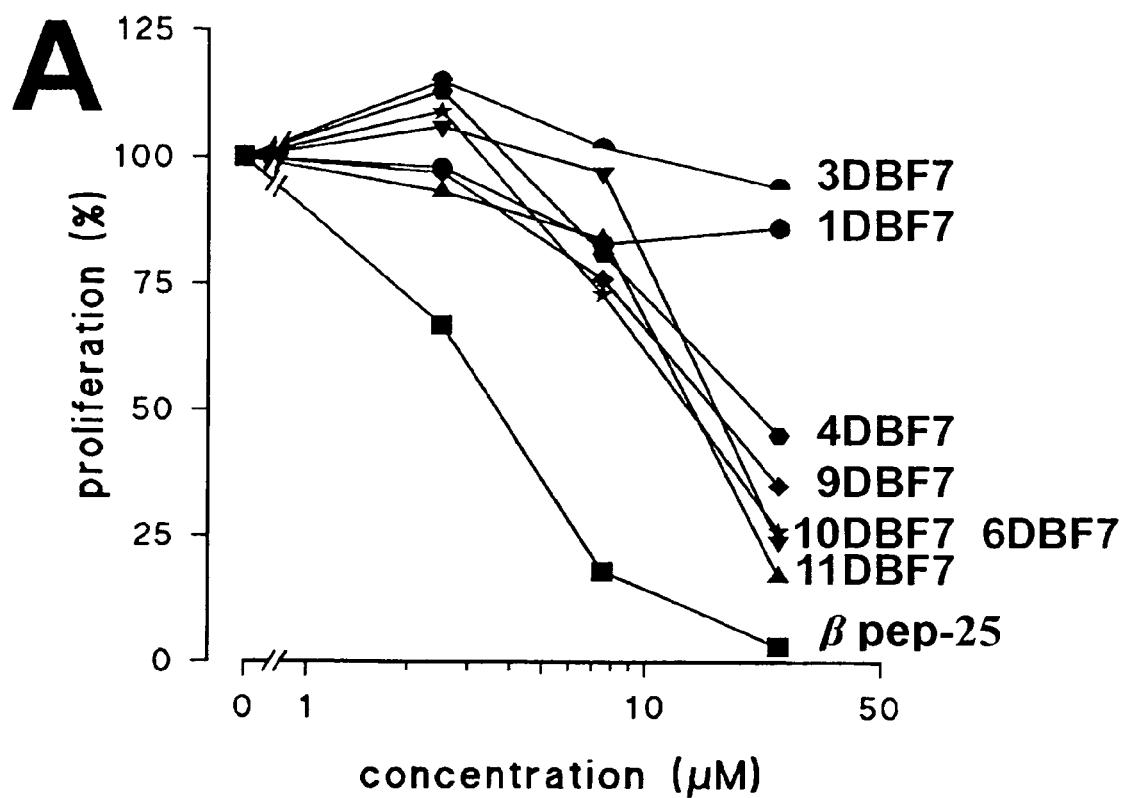
FIG. 3. Anti-proliferative effects of DBF analogs on bFGF-activated EC are plotted as dose response curves.

In endothelial cell (EC) proliferation assays, it was demonstrated that 11DBF7, as well as a number of shorter analogs, are effective at inhibiting EC growth. Dose response curves for all xDBF7 analogs are exemplified in FIG. 3, and IC$_{50}$ values for all DBF analogs (i.e., partial peptide mimetics) and percent inhibition of EC growth at 25 μM are given in Table 1. Compared to parent β-pep-25 (IC50, 3 μM), most DBF analogs, although slightly less active (IC50 about 10 μM), do perform relatively well in this assay. This may, in part, be explained by their decreased size. In addition, some of the analogs are missing residues identified by alanine scanning as being functionally important (e.g., $L_5$ and $I_3$). Nonetheless, a number of these shorter analogs remain reasonably active, and it appears that the N-terminal hexapeptide SVQMKL (SEQ ID NO:5) and C-terminal tetrapeptide IIVK (SEQ ID NO:3) enhance anti-angiogenic activity.

Angiostatic potential was further demonstrated in vitro in the collagen gel-based sprout formation assay (R. P. Dings et al., Cancer Res., 63, 382-385 (2003)). Whereas the control showed numerous sprouts, treatment with βpep-25, 11DBF7 and 6DBF7 all demonstrated highly reduced sprouting (data not shown). Quantitative results for all analogs are given in Table 1. In general, reducing the number of amino acid residues in the β-strands led to reduced inhibition of sprout formation, comparable with the proliferation assay. However, some analogs were active and even one of the shortest analogs, 6DBF7, had a significant inhibitory effect on tube formation. The kinetics of inhibition using DBF analogs, moreover, were the same as those for βpep-25 (data not shown).

DBF Analogs Inhibit Tumor Growth in Mice.

Figure 4:
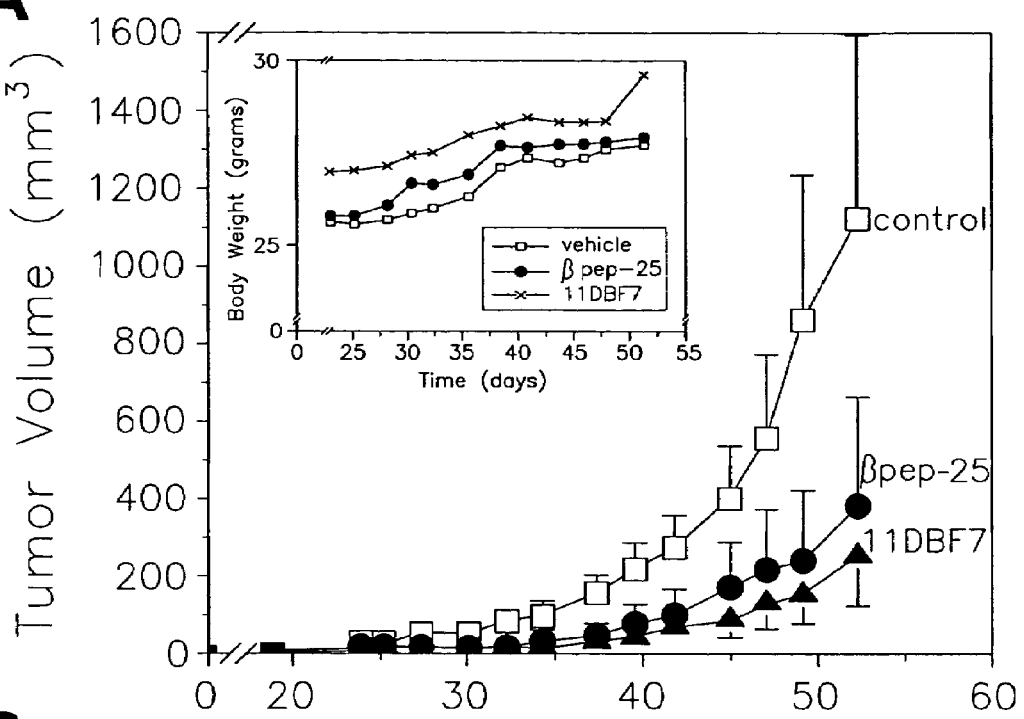
FIG. 4. MA148 tumor bearing mice were treated with the optimal dose of βpep-25 (10 mg/kg/day) or equivalent doses of 11DBF7 or 6DBF7.
Figure 4:
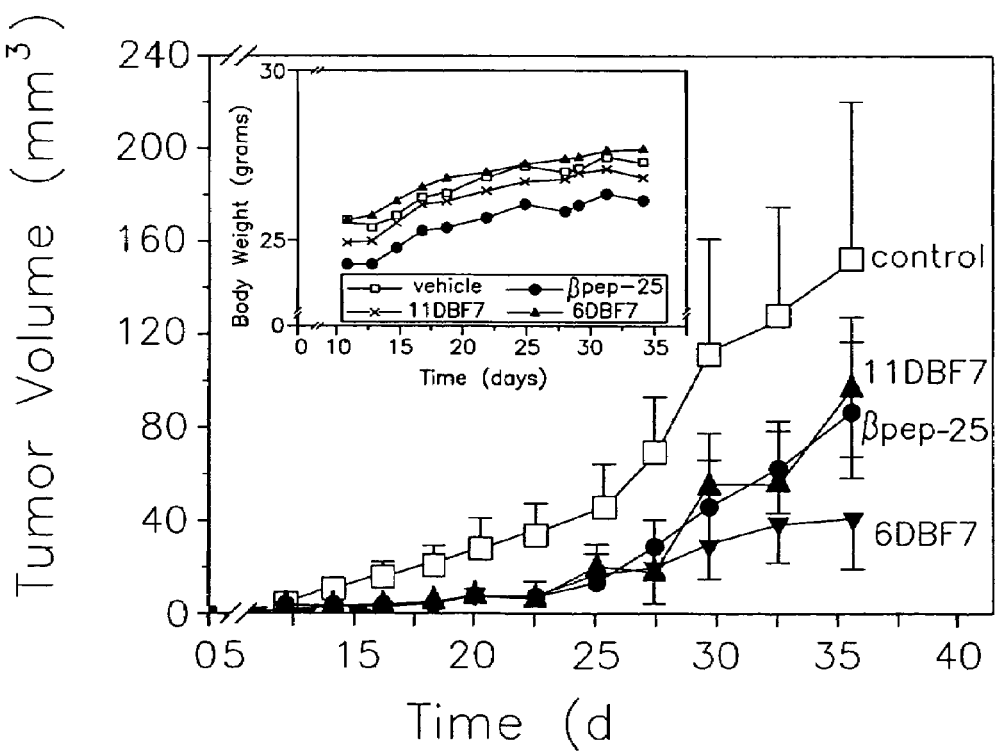

Because specific use of an anti-angiogenic agent is in the area of tumor biology, the in vivo efficacy of two of the most in vitro active DBF analogs, 11DBF7 and 6DBF7, were assessed along with βpep-25 as a positive control, in the MA148 xenograft ovarian carcinoma tumor model in athymic mice as previously described in R. P. Dings et al., Cancer Res., 63, 382-385 (2003). Initial experiments using this model administered the DBF analog, 11DBF7, subcutaneously via mini-pumps implanted at the time of inoculation with the tumor cell line. This prevention model demonstrated that treatment of tumor forming animals with 11DBF7 resulted in inhibition of tumor growth (FIG. 4A). Surprisingly, 11DBF7 functioned, on average, slightly better than βpep-25 by reducing tumor volume by up to 90% relative to control animals.

In further experiments, treatment was initiated seven days following inoculation with tumor cells to allow establishment of small tumors prior to the start of treatment. Using this protocol, βpep-25, 11DBF7, as well as 6DBF7, were tested and were found to inhibit tumor growth by up to 70% during the course of treatment and by about 50% at the end of the four-week administration period (day 35) (FIG. 4B). The rate of tumor growth then began to increase, but remained at about 50% ten days post-treatment when animals were sacrificed for analysis of tumor tissue. Interestingly, the smaller DBF analog, 6DBF7, was observed to be slightly more effective at inhibiting tumor growth than βpep-25 or 11DBF7. On day 35, for example, 6DBF7 sustained tumor growth inhibition to more than 70% relative to tumors from control animals (FIG. 4B).

In vivo anti-angiogenic potential was demonstrated by staining tumor cross-sections from treated animals with fluorescently-labeled anti-CD31 antibody used immunohistochemically to identify blood vessels. Vessel density, relative to control, was significantly reduced by treatment with βpep-25, 11DBF7, or 6DBF7. In addition, these anti-angiogenic compounds had a significant effect as well on vessel architecture, demonstrating a drop in the number of end points, branch points and vessel length (Table 2). In addition, anti-angiogenic treatment also reduced the rate of proliferation of tumor cells as determined by immunohistochemical staining of PCNA in cryosections of tumors (Table 2). As a result of angiogenic inhibition, the number of apoptotic tumor cells increased from 311±103 in the control, to 620±146 and 851±162 in βpep25 and 6DBF7 treated animals, respectively.

TABLE 2

Microvessel density and proliferation rate in tumors of treated mice

| | Proliferation[a] | Vessel Density[b] | End Points[c] | Branch Points[d] | Vessel Length[e] |
|---|---|---|---|---|---|
| Vehicle | 848 ± 104 | 5858 ± 656 | 26.2 ± 2.2 | 7.6 ± 1.4 | 5.9 ± 0.7 |
| βpep-25 | 414 ± 44 | 2245 ± 329 | 22.9 ± 2.2 | 2.1 ± 0.6 | 0.9 ± 0.3 |
| 11DBF7 | 553 ± 75 | 2879 ± 385 | 21.2 ± 3.3 | 3.1 ± 0.9 | 3.0 ± 0.6 |
| 6DBF7 | 501 ± 68 | 2213 ± 256 | 21.7 ± 2.6 | 2.3 ± 1.1 | 2.5 ± 0.4 |

[a] After binarization of the images of the PCNA-staining, proliferation was estimated by scoring the total number of white pixels per field.
[b] After binarization of the images of the CD31-staining, microvessel density was estimated by scoring the total number of white pixels per field.
[c] Mean number of vessel end points as determined after skeletonization of the images (R. Wild et al., Microvasc. Res., 59, 368-376 (2000)).
[d] Mean number of vessel branch points/nodes per image.
[e] Mean total vessel length per image.
All results are expressed as mean pixel counts per image (±standard error).

In all in vivo experiments, treatment with βpep-25, 11DBF7, and 6DBF7 did not show any sign of toxicity as assessed by unaltered behavior and normal weight gain during experiments (data not shown). Moreover, hematocrit and creatinine levels in treated animals were normal relative to control, indicating the absence of toxicity to bone marrow and kidney. Macro- and microscopic morphology of internal organs on autopsy were also observed to be normal within all experimental groups of animals.

CONCLUSION

In summary, amino acid residues that promote βpep-25's angiostatic activity have been identified, and partial peptide mimetics of βpep-25 have been designed and synthesized. The more effective mimetics carried only 13 of its 33 amino acid residues and showed that the partial peptide mimetic is an effective anti-angiogenic agent both in vitro and in vivo. Moreover, whereas as in vitro activity is somewhat less than that of βpep-25, in vivo activity appears to be improved, suggesting increased bioavailabilty with DBF analogs. Both the significant reduction in the number of residues required to promote angiostatic activity and the use of an organic β-sheet-inducing scaffold allows for the development of an orally-active, small molecule mimetic of an anti-angiogenic protein.

The DBF analogs not tested in these analyses would be expected by one of skill in the art to provide some activity in at least one of the assays due to the homology of their structures. Also, although not shown, DBF analogs of the type described herein demonstrate some bacteriocidal activity and some endotoxin neutralizing activity. Furthermore, because of the results shown herein, DBF analogs of the type described herein would be expected by one of skill in the art to inhibit TNF-a levels, promote inter-cellular adhesion molecule (ICAM) expression, and inhibit inter-cellular adhesion molecule (ICAM) expression down regulation. Also, particularly because of the results with respect to the inhibition of angiogenesis, DBF analogs of the type described herein would be expected by one of skill in the art to inhibit pathologic disorders such as atherosclerosis, restenosis, diabetic retinopathy, neovascular glaucoma, rheumatoid arthritis, and endometriosis.

All references cited herein are incorporated by reference, in their entirety, into this text. Although the invention has been described in the context of particular embodiments, it is intended that the scope of coverage of the patent be limited only by reference to the following claims.

Sequence Listing Free Text Amino Acis Sequence og Peptides

βpep-25 (SEQ ID NO:1)
ANIKLSVQMKLFKRHLKWKIIVKLNDGRELSLD
(SEQ ID NO:2)
IIVKLND
(SEQ ID NO:3)
IIVK
(SEQ ID NO:4)
QMKL
(SEQ ID NO:5)
SVQMKL
(SEQ ID NO:6)
IKLSVQMKL
(SEQ ID NO:7)
NIKLSVQMKL
(SEQ ID NO:8)
ANIKLSVQMKL
(SEQ ID NO:9)
IIVKLN

What is claimed is:

1. A partial peptide mimetic comprising a first amino acid sequence consisting of ANIKLSVQMKL (SEQ ID NO:8) or a segment thereof, a second amino acid sequence consisting of IIVKLND (SEQ ID NO:2) or a segment thereof, and a β-turn inducing scaffold bonded between the first and second amino acid sequences, wherein the segment of SEQ ID NO:8 is one in which a deletion has been made at the N-terminus by 1, 2, 3, 4, 5, 6, 7, or 8 residues, and wherein the segment of SEQ ID NO:2 is one in which a deletion has been made at the C-terminus by 1, 2, 3, 4, 5, or 6 residues.

2. A partial peptide mimetic comprising:
a first amino acid sequence;
a second amino acid sequence; and
a β-turn inducing scaffold bonded between the first and second amino acid sequences;
wherein the first amino acid sequence consists of an amino acid sequence selected from the group consisting of ANIKLSVQMKL (SEQ ID NO:8) and a segment of SEQ ID NO:8;
wherein the second amino acid sequence consists of an amino acid sequence selected from the group consisting of IIVKLND (SEQ ID NO:2) and a segment of SEQ ID NO:2;
wherein a segment of SEQ ID NO:8 consists of at least three contiguous amino acids of SEQ ID NO:8;
wherein a segment of SEQ ID NO:2 consists of at least one contiguous amino acid of SEQ ID NO:2; and
wherein segment provides the partial peptide mimetic with at least one of the following activities: inhibition of endothelial cell proliferation in vitro at an IC50 level of less than 80 mM; inhibition of angiogenesis in vitro at a level of less than 85% sprouting in a collagen gel-based assay; or reduction in tumor volume in vivo by at least 25% relative to a control at the end of an administration period.

3. The partial peptide mimetic of claim 2 wherein the first amino acid sequence consists of a segment of SEQ ID NO:8, from which a deletion has been made at the N-terminus of SEQ ID NO:8 by 1, 2, 3, 4, 5, 6, 7, or 8 residues.

4. The partial peptide mimetic of claim 2 wherein the first amino acid sequence consists of an amino acid selected from the group consisting of MKL, QMKL (SEQ ID NO:4), SVQMKL (SEQ ID NO:5), IKLSVQMKL (SEQ ID NO:6), NIKLSVQMKL (SEQ ID NO:7), and ANIKLSVQMKL (SEQ ID NO:8).

5. The partial peptide mimetic of claim 2 wherein the first amino acid sequence is ANIKLSVQMKL (SEQ ID NO:8) and the second amino acid sequence is IIVKLND (SEQ ID NO:2).

6. The partial peptide mimetic of claim 1 wherein the second amino acid sequence consists of a segment of SEQ ID NO:2 from which a deletion has been made at the C-terminus of SEQ ID NO:2 by 1, 2, 3, 4, 5, or 6 residues.

7. The partial peptide mimetic of claim 1 wherein the second amino acid sequence consists of an amino acid sequence selected from the group consisting of I, IIVK (SEQ ID NO:3), IIVKLN (SEQ ID NO:9) and IIVKLND (SEQ ID NO:2).

8. The partial peptide mimetic of claim 7 wherein the first amino acid sequence consists of an amino acid sequence selected from the group consisting of MKL, QMKL (SEQ ID NO:4), SVQMKL (SEQ ID NO:5), IKLSVQMKL (SEQ ID NO:6), NIKLSVQMKL (SEQ ID NO:7), and ANIKLSVQMKL (SEQ ID NO:8).

9. The partial peptide mimetic of claim 1 wherein the β-turn inducing scaffold is a dibenzofuran-containing scaffold.

10. The partial peptide mimetic of claim 1, wherein the partial peptide mimetic has at least one of the following activities: inhibition of endothelial cell proliferation in vitro at an IC50 level of less than 80 µM; inhibition of angiogenesis in vitro at a level of less than 85% sprouting in a collagen gel-based assay; or reduction in tumor volume in vivo by at least 25% relative to a control at the end of an administration period.

11. A partial peptide mimetic selected from the group consisting of:
ANIKLSVQMK (SEQ ID NO:8) and IIVKLND (SEQ ID NO:2), with a β-turn inducing scaffold bonded therebetween;
NIKLSVQMKL (SEQ ID NO:7) and IIVKLND (SEQ ID NO:2), with a β-turn inducing scaffold bonded therebetween;
JKLSVQMKL (SEQ ID NO:6) and IIVKLND (SEQ ID NO:2), with a β-turn inducing scaffold bonded therebetween;
SVQMKL (SEQ ID NO:5) and IIVKLND (SEQ ID NO:2), with a β-turn inducing scaffold bonded therebetween;
QMKL (SEQ ID NO:4) and IIVKLND (SEQ ID NO:2), with a β-turn inducing scaffold banded therebetween;
MKL and IIVKLND (SEQ ID NO:2), with a β-turn inducing scaffold bonded therebetween;
L and IIVKLND (SEQ ID NO:2), with a β-turn inducing scaffold bonded therebetween;
ANIKLSVQMKL (SEQ ID NO:8) and IIVKLN (SEQ ID NO:9), with a β-turn inducing scaffold bonded therebetween;
ANIKLSVQMKL (SEQ ID NO:8) and IIVK (SEQ ID NO:3), with a β-turn inducing scaffold bonded therebetween;
ANIKLSVQMK (SEQ ID NO:8) and I, with a β-turn inducing scaffold bonded therebetween;
SVQMKL (SEQ ID NO:5) and IIVK (SEQ ID NO:9), with a β-turn inducing scaffold bonded therebetween;
SVQMKL (SEQ ID NO:5) and IIVK (SEQ ID NO:3), with a β-turn inducing scaffold bonded therebetween;

SVQMKL (SEQ ID NO:5) and IIV, with a β-turn inducing scaffold bonded therebetween;
SVQMKL (SEQ ID NO:5) and II, with a β-turn inducing scaffold bonded therebetween; and
SVQMKL (SEQ ID NO:5) and I, with a β-turn inducing scaffold bonded therebetween.

12. The partial peptide mimetic of claim 11 wherein the partial peptide mimetic has at least one of the following activities: inhibition of endothelial cell proliferation in vitro at an IC50 level of less than 80 μM; inhibition of angiogenesis in vitro at a level of less than 85% sprouting in a collagen gel-based assay; or reduction in tumor volume in vivo by at least 25% relative to a control at the end of an administration period.

13. A method far inhibiting endothelial cell proliferation, the method comprising contacting cells with an amount of a composition effective to inhibit endothelial cell proliferation, wherein the composition comprises a partial peptide mimetic of any one of claims 1, 2, 11.

14. The method of claim 13 wherein the contacting step occurs in vitro.

15. The method of claim 13 wherein the contacting step occurs in vivo.

16. The method of claim 13 wherein the cells are present in a cell culture, a tissue, an organ, or an organism.

17. The method of claim 13 wherein the cells arc mammalian cells.

18. The method of claim 13 wherein the cells are human cells.

19. A method for inhibiting angiogenesis, the method comprising contacting cells with an amount of a composition effective to inhibit angiogenesis, the composition comprising a partial peptide mimietic of any one of claims 1, 2, 11.

20. The method of claim 19 wherein the contacting step occurs in vitro.

21. The method of claim 19 wherein the contacting step occurs in vivo.

22. The method of claim 19 wherein the cells are present in a cell culture, a tissue, an organ, or an organism.

23. The method of claim 19 wherein the cells are mammalian cells.

24. The method of claim 19 wherein the cells are human cells.

25. A method for inhibiting tumorigenesis in a patient, the method comprising administering to the patient a therapeutically effective amount of a composition comprising a partial peptide mimetic of any one of claims 1, 2, 11.

* * * * *

UNITED STATES PATENT AND TRADEMARK OFFICE
CERTIFICATE OF CORRECTION

PATENT NO.       : 7,339,023 B2                                           Page 1 of 1
APPLICATION NO. : 11/346504
DATED            : March 4, 2008
INVENTOR(S)      : Mayo et al.

It is certified that error appears in the above-identified patent and that said Letters Patent is hereby corrected as shown below:

Column 30, Line 43
Delete "JKLSVQMKL" and insert --IKLSVQMKL--

Signed and Sealed this

Twenty-fourth Day of June, 2008

JON W. DUDAS
*Director of the United States Patent and Trademark Office*

```
                        SEQUENCE LISTING

<160> NUMBER OF SEQ ID NOS: 17

<210> SEQ ID NO 1
<211> LENGTH: 33
<212> TYPE: PRT
<213> ORGANISM: ARTIFICIAL SEQUENCE
<220> FEATURE:
<223> OTHER INFORMATION: Artificially Synthesized Peptide

<400> SEQUENCE: 1

Ala Asn Ile Lys Leu Ser Val Gln Met Lys Leu Phe Lys Arg His Leu
1               5                   10                  15

Lys Trp Lys Ile Ile Val Lys Leu Asn Asp Gly Arg Glu Leu Ser Leu
            20                  25                  30

Asp

<210> SEQ ID NO 2
<211> LENGTH: 7
<212> TYPE: PRT
<213> ORGANISM: ARTIFICIAL SEQUENCE
<220> FEATURE:
<223> OTHER INFORMATION: Artificially Synthesized Peptide

<400> SEQUENCE: 2

Ile Ile Val Lys Leu Asn Asp
1               5

<210> SEQ ID NO 3
<211> LENGTH: 4
<212> TYPE: PRT
<213> ORGANISM: ARTIFICIAL SEQUENCE
<220> FEATURE:
<223> OTHER INFORMATION: Artificially Synthesized Peptide

<400> SEQUENCE: 3

Ile Ile Val Lys
1

<210> SEQ ID NO 4
<211> LENGTH: 4
<212> TYPE: PRT
<213> ORGANISM: ARTIFICIAL SEQUENCE
<220> FEATURE:
<223> OTHER INFORMATION: Artificially Synthesized Peptide

<400> SEQUENCE: 4

Gln Met Lys Leu
1
```

```
<210> SEQ ID NO 5
<211> LENGTH: 6
<212> TYPE: PRT
<213> ORGANISM: ARTIFICIAL SEQUENCE
<220> FEATURE:
<223> OTHER INFORMATION: Artificially Synthesized Peptide

<400> SEQUENCE: 5

Ser Val Gln Met Lys Leu
1               5

<210> SEQ ID NO 6
<211> LENGTH: 9
<212> TYPE: PRT
<213> ORGANISM: ARTIFICIAL SEQUENCE
<220> FEATURE:
<223> OTHER INFORMATION: Artificially Synthesized Peptide

<400> SEQUENCE: 6

Ile Lys Leu Ser Val Gln Met Lys Leu
1               5

<210> SEQ ID NO 7
<211> LENGTH: 10
<212> TYPE: PRT
<213> ORGANISM: ARTIFICIAL SEQUENCE
<220> FEATURE:
<223> OTHER INFORMATION: Artificially Synthesized Peptide

<400> SEQUENCE: 7

Asn Ile Lys Leu Ser Val Gln Met Lys Leu
1               5                   10

<210> SEQ ID NO 8
<211> LENGTH: 11
<212> TYPE: PRT
<213> ORGANISM: ARTIFICIAL SEQUENCE
<220> FEATURE:
<223> OTHER INFORMATION: Artificially Synthesized Peptide

<400> SEQUENCE: 8

Ala Asn Ile Lys Leu Ser Val Gln Met Lys Leu
1               5                   10

<210> SEQ ID NO 9
<211> LENGTH: 6
<212> TYPE: PRT
<213> ORGANISM: ARTIFICIAL SEQUENCE
<220> FEATURE:
<223> OTHER INFORMATION: Artificially Synthesized Peptide

<400> SEQUENCE: 9

Ile Ile Val Lys Leu Asn
1               5

<210> SEQ ID NO 10
<211> LENGTH: 12
<212> TYPE: PRT
<213> ORGANISM: ARTIFICIAL SEQUENCE
<220> FEATURE:
<223> OTHER INFORMATION: Artificially Synthesized Peptide

<400> SEQUENCE: 10

Ala Asn Ile Lys Leu Ser Val Gln Met Lys Leu Phe
1               5                   10

<210> SEQ ID NO 11
```

```
<211> LENGTH: 12
<212> TYPE: PRT
<213> ORGANISM: ARTIFICIAL SEQUENCE
<220> FEATURE:
<223> OTHER INFORMATION: Artificially Synthesized Peptide

<400> SEQUENCE: 11

Lys Leu Ser Val Gln Met Lys Leu Phe Lys Arg His
1               5                   10

<210> SEQ ID NO 12
<211> LENGTH: 12
<212> TYPE: PRT
<213> ORGANISM: ARTIFICIAL SEQUENCE
<220> FEATURE:
<223> OTHER INFORMATION: Artificially Synthesized Peptide

<400> SEQUENCE: 12

Val Gln Met Lys Leu Phe Lys Arg His Leu Lys Trp
1               5                   10

<210> SEQ ID NO 13
<211> LENGTH: 12
<212> TYPE: PRT
<213> ORGANISM: ARTIFICIAL SEQUENCE
<220> FEATURE:
<223> OTHER INFORMATION: Artificially Synthesized Peptide

<400> SEQUENCE: 13

Lys Leu Phe Lys Arg His Leu Lys Trp Lys Ile Ile
1               5                   10

<210> SEQ ID NO 14
<211> LENGTH: 12
<212> TYPE: PRT
<213> ORGANISM: ARTIFICIAL SEQUENCE
<220> FEATURE:
<223> OTHER INFORMATION: Artificially Synthesized Peptide

<400> SEQUENCE: 14

Lys Arg His Leu Lys Trp Lys Ile Ile Val Lys Leu
1               5                   10

<210> SEQ ID NO 15
<211> LENGTH: 12
<212> TYPE: PRT
<213> ORGANISM: ARTIFICIAL SEQUENCE
<220> FEATURE:
<223> OTHER INFORMATION: Artificially Synthesized Peptide

<400> SEQUENCE: 15

Leu Lys Trp Lys Ile Ile Val Lys Leu Asn Asp Gly
1               5                   10

<210> SEQ ID NO 16
<211> LENGTH: 12
<212> TYPE: PRT
<213> ORGANISM: ARTIFICIAL SEQUENCE
<220> FEATURE:
<223> OTHER INFORMATION: Artificially Synthesized Peptide

<400> SEQUENCE: 16

Lys Ile Ile Val Lys Leu Asn Asp Gly Arg Glu Leu
1               5                   10

<210> SEQ ID NO 17
<211> LENGTH: 12
```

-continued

```
<212> TYPE: PRT
<213> ORGANISM: ARTIFICIAL SEQUENCE
<220> FEATURE:
<223> OTHER INFORMATION: Artificially Synthesized Peptide

<400> SEQUENCE: 17

Val Lys Leu Asn Asp Gly Arg Glu Leu Ser Leu Asp
1               5                   10
```